(12) United States Patent
Fan et al.

(10) Patent No.: US 9,381,194 B2
(45) Date of Patent: Jul. 5, 2016

(54) PHARMACOLOGICAL CHAPERONES FOR TREATING OBESITY

(75) Inventors: Jian-Qiang Fan, Demarest, NJ (US); Kenneth Valenzano, East Brunswick, NJ (US); Gary Lee, West Windsor, NJ (US); Michel Bouvier, Montreal (CA); Patricia René, Montréal (CA)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 12/534,665

(22) Filed: Aug. 3, 2009

(65) Prior Publication Data
US 2009/0312345 A1 Dec. 17, 2009

Related U.S. Application Data

(63) Continuation of application No. 11/446,429, filed on Jun. 2, 2006, now abandoned.

(60) Provisional application No. 60/687,648, filed on Jun. 3, 2005, provisional application No. 60/799,968, filed on May 12, 2006.

(51) Int. Cl.
*A61K 31/497* (2006.01)
*A61K 31/4725* (2006.01)
*A61K 31/505* (2006.01)

(52) U.S. Cl.
CPC .............. *A61K 31/497* (2013.01); *A61K 31/505* (2013.01)

(58) Field of Classification Search
None
See application file for complete search history.

(56) References Cited

U.S. PATENT DOCUMENTS

| 5,985,824 A | 11/1999 | Cheng et al. |
| 6,270,954 B1 | 8/2001 | Welch et al. |
| 6,274,597 B1 | 8/2001 | Fan et al. |

(Continued)

FOREIGN PATENT DOCUMENTS

| JP | 2004-534850 | 11/2004 |
| WO | WO-93/13768 | 7/1993 |

(Continued)

OTHER PUBLICATIONS

Ozcan et al., Endoplasmic reticulum stress plays a central role in development of leptin resistance, Cell Metab. 9(1):35-51, Jan. 2009.*

(Continued)

*Primary Examiner* — Claire Kaufman
(74) *Attorney, Agent, or Firm* — Servilla Whitney LLC; Michelle A. Cristaldi; Rory P. Alegria

(57) ABSTRACT

The invention relates to methods of enhancing normal melanocortin-4 receptor (MC4R) activity, and to enhancing activity of an MC4R having a mutation which affects protein folding and/or processing of the MC4R. The invention provides a method of treating an individual having a condition in which increased activity of an MC4R at the cell surface would be beneficial, for example in obesity, by administering an effective amount of a pharmacological chaperone for the MC4R. The invention provides MC4R pharmacological chaperones which enhance the activity of MC4R. The invention further provides a method of screening to identify pharmacological chaperones which enhance folding of an MC4R in the endoplasmic reticulum (ER), in order to enhance the activity of the MC4R at the cell surface.

16 Claims, 17 Drawing Sheets

MC4R ANTAGONISTS

(56) References Cited

U.S. PATENT DOCUMENTS

| | | | |
|---|---|---|---|
| 6,344,475 | B1 | 2/2002 | Caplan et al. |
| 6,583,158 | B1 | 6/2003 | Fan et al. |
| 6,960,646 | B2 | 11/2005 | Bednarek |
| 2006/0183789 | A1 | 8/2006 | Rajachandran et al. |
| 2008/0269217 | A1 * | 10/2008 | Vos et al. |

FOREIGN PATENT DOCUMENTS

| | | |
|---|---|---|
| WO | WO-95/05810 | 3/1995 |
| WO | WO 0032175 A2 * | 6/2000 |
| WO | WO-02/28348 | 4/2002 |
| WO | WO-02/062766 | 8/2002 |
| WO | WO 02062722 A2 * | 8/2002 |
| WO | WO-03/038036 | 5/2003 |
| WO | WO-2004/069859 | 12/2004 |

OTHER PUBLICATIONS

Yam et al., Pharmacological chaperone corrects lysosomal storage in Fabry disease caused by trafficking-incompetent variants, Am. J. Physiol. Cell Physiol. 290: C1076-C1082, 2006.*

Arasasingham et al., Structure-activity relationship of (1-aryl-2piperzinylethyl)piperazines:antagonists for the AGRP/melanocortin receptor binding, J. Med. Chem. 46:9-11, 2003.*

Richardson et al., Synthesis and structure-activity relationship of novel arylpiperazines as potent and selective agonists of the melanocortin subtype-4 receptor, J. Med. Chem. 47:744-755, 2004.*

Pedemonte et al., Small-molecule correctors of defective delta-F508-CFTR celular processing identified by high-throughput screening, J. Clin. Invest. 115(9):2564-2571, Sep. 2005.*

Petaja-Repo et al., Ligands act as pharmacological chaperones and increase the efficiency of delta opiod receptor maturation, EMBO J. 21(7):1628-1637, 2002.*

Kolk et al., The role of leptin and ghrelin in the regulation of food intake and body weight in humans: a review, Obesity Rev. 8:21-34, 2007.*

Granell et al., Obesity-linked variants of melanocortin-4 receptor are misfolded in the endoplasmic reticulum and can be rescued to the cell surface by a chemical chaperone, Mol. Endocrinol. 24:1803-1821, 2010.*

Kask et al., Long-term administration of MC4 receptor antagonist HS014 causes hyperphagia and obesity in rats, Neuroreport, 10(4):707-711, 1999.*

Nijenhuis et al. Poor cell surface expression of human melanocortin-4 receptor mutations associated with obesity, J. Biol. Chem. 278(25):22939-45, 2003.*

Dong et al., Functional rescue of obesity-causing human melanocortin-4 receptor mutants:insights for pharmacological chaperon drugs, Transl. Med. 3(2):e123, 2013.*

Fani et al., The melanocortin-4 receptor as target for obesity treatment: a systemic review of emerging pharmacological therapy options, Int. J. Obesity, 38:163-169, 2014.*

Haskell-Luevano et al., Structure activity stuides of the melanocortin-4 receptor by in vitro mutagenesis: identification of agouit-related protein (AGRP), melanocortin agonist and synthetic peptide antafonist interaction detenimants, Biochem. 40:6164-79, 2001.*

René et al. Pharmacological chaperones restore funciton to MC4R mutants responsible for severe early-onset obesity, J. Pharmacol. Exp. Ther. 335(3):530-532, 2010.*

Ruvinov et al., Monovalent Cations Partially Repair a Conformational Defect in a Mutant Tryptophan Synthase α2β2 Complex (β-E109A); J. Biol. Chem, 1995; 270: 17333-38.

Final Office Action in U.S. Appl. No. 11/446,429, dated Dec. 3, 2008, 8 pages.

Non-Final Office Action in U.S. Appl. No. 11/446,429, dated Apr. 2, 2008, 10 pages.

Partial European Search Report in EP15153180, dated Jul. 31, 2015, 6 pages.

Bernier, Virginie, et al., Functional Rescue of the Constitutively Internalized V2 Vasopressin Receptor Mutant R137H by the Pharmacological Chaperone Action of SR49059, Molecular Endocrinology vol. 18 No. 8 2004, 2074-2084.

Bernier, Virginie, et al., Pharmacological chaperone action on G-protein-coupled receptors, Current Opinion in Pharmacology vol. 4 2004, 528-533.

Burrows, Jon A., et al., Chemical chaperones mediate increased secretion of mutant alpha1-antitrypsin (alpha1-AT) Z: A potential pharmacological strategy for prevention of liver injury and emphysema in alpha1-AT deficiency, PNAS vol. 97 No. 4 Feb. 15, 2000, 1796-1801.

Chaki, Shigeyuki, et al., Anxiolytic-Like and Antidepressant-Like Activities of MCL0129 (1-[(S)-2-(4-Fluorophenyl)-2-(4-isopropylpiperadin-1-yl)ethyl]-4-[4-(2-methoxynaphthalen-1-yl)butyl]piperazine), a Novel and Potent Nonpeptide Antagonist of the Melanocortin-4 Receptor, The Journal of Pharmacology and Experimental Therapeutics, vol. 304 No. 2 2003, 818-826.

Chen, Chen, et al., 4-{(2R)-[3-Aminopropionylamido]-3-(2,4-dichlorophenyl)propionyl}-1-{2-[(2-thienyl)ethylaminomethyl]phenyl}piperazine as a Potent and Selective Melanocortin-4 Receptor Antagonist—Design, Synthesis, and Characterization, J. Med. Chem. vol. 47 2004, 6821-6830.

Conn, Michael P., et al., Protein Folding as Post-translations Regulation: Evolution of a Mechanism for Controlled Plasma Membrane Expression of a GPCR, Molecular Endocrinology Manuscript 2006, 20 pages.

Conn, Michael P., et al., Protein Origami: Therapeutic Rescue of Misfolded Gene Products, Molecular Interventions: Mutant Protein Rescue vol. 2, Iss. 5 Sep. 2002, 209-316.

Fan, Jun, et al., A Point Mutation in the Human Melanin Concentrating Hormone Receptor 1 Reveals an Important Domain for Cellular Trafficking, Molecular Endocrinology vol. 19 No. 10 2005, 2579-2590.

Foster, Barbara A., et al., Pharmacological Rescue of Mutant p53 Conformation and Function, Science vol. 286 Dec. 24, 1999, 2507-2510.

Janovick, Jo Ann, et al., Structure-Activity Relations of Successful Pharmacologic Chaperones for Rescue of Naturally Occurring and Manufactured Mutants of the Gonadotropin-Releasing Hormone Receptor, The Journal of Pharmacology and Experimental Therapeutics, vol. 305 No. 2 2003, 608-614.

Leanos-Miranda, Alfredo, et al., In Vitro Coexpression and Pharmacological Rescue of Mutant Gonadotropic-Releasing Hormone Receptors Causing Hypogonadotropic Hypogonadism in Humans Expressing Compound Heterozygous Alleles, The Journal of Clinical Endocrinology & Metabolism vol. 90 No. 5 2005, 3001-3008.

Loo, Tip W., et al., Correction of Defective Protein Kinesis of Human P-gylcoprotein Mutants by Substrates and Modulators, The Journal of Biological Chemistry vol. 272 No. 2 1997, 709-712.

Lubrano-Berthelier, Cecile, et al., Intracellular retention is a common characteristic of childhood obesity-associated MC4R mutations, Human Molecular Genetics vol. 12 No. 2 2002, 145-153.

Morello, Jean-Pierre, et al., Pharmacological chaperones: a new twist on receptor folding, TiPS—Viewpoint vol. 21 Dec. 2000, 466-469.

Pontillo, Joseph, et al., Piperazinebenxylamines as potent and selective antagonists of the human melanocortin-4 receptor, Bioorganic & Medicinal Chemistry Letters vol. 14 2004, 5605-5609.

Tran, Joe A., et al., Identification of agonists and antagonists of the human melanocortin-4 receptor from piperazinebenzylamines, Bioorganic & Medicinal Chemistry Letters vol. 15 2005, 833-837.

Ulloa-Aguirre, Alfredo, et al., Pharmacologic Rescue of Conformationally-Defective Proteins: Implications for the Treatment of Human Disease, Traffic vol. 5 2004, 821-837.

Xiang, Zhimin, et al., Pharmacological Characterization of 40 Human Melanocortin-4 Receptor Polymorphisms with the Endogenous Proopiomelanocortin-Derived Agonists and the Agouti-Related Protein (AGRP) Antagonist, Biochemistry vol. 45 2006, 7277-7288.

Zhou, Zhengfeng, et al., Correction of Defective Protein Trafficking of a Mutant HERG Potassium Channel in Human Long QT Syndrome, Journal of Biological Chemistry, vol. 274 No. 44 1999, 31123-31126.

* cited by examiner

MC4R AGONISTS

MC4R ANTAGONISTS

FIG. 14
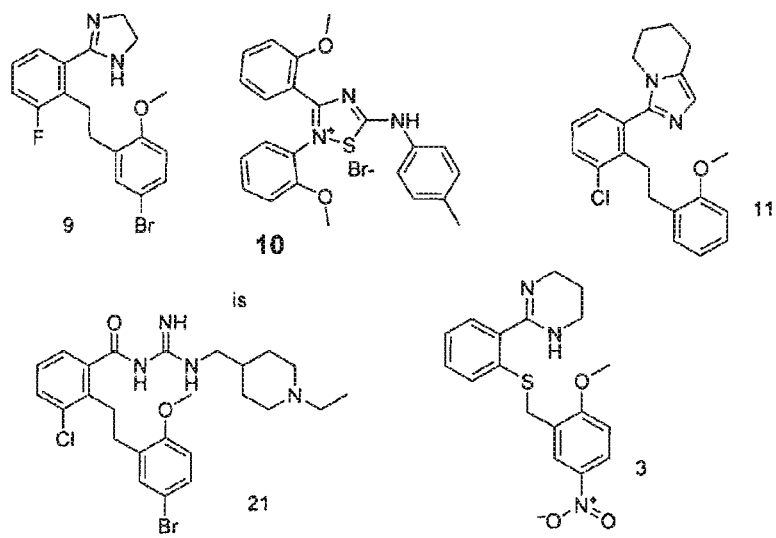
where X and Y are respectively and independantly H, F, Cl, Br, I, or NO₂;
A is  or no bond;
B -F are respectively and independantly C, N, or S;
R₁ is a heterocyclyl, alkoxy, or substituted carbamoyl;
R₂ is H or -OCH₃; and
R₃ is substituted amino
When R₁ is a heterocyclic, the heterocyclic preferably includes 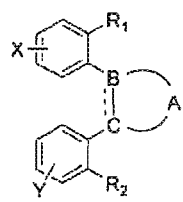

FIG. 15
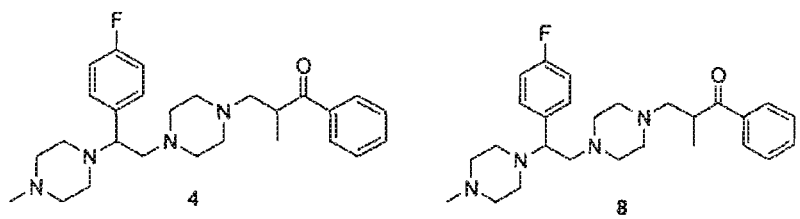
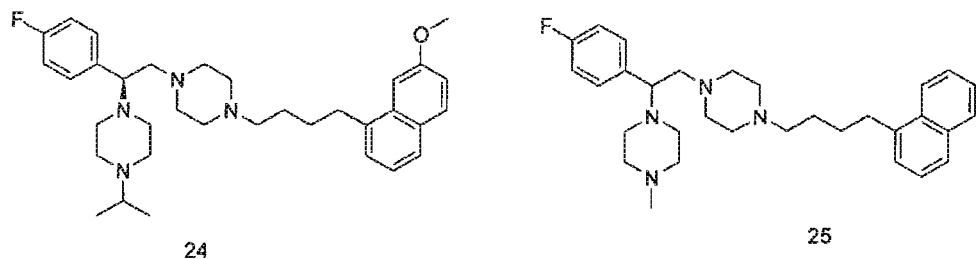
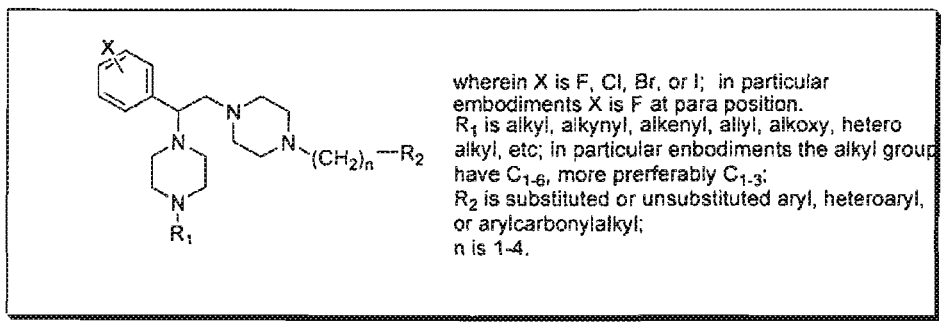
wherein X is F, Cl, Br, or I; in particular embodiments X is F at para position.
R₁ is alkyl, alkynyl, alkenyl, allyl, alkoxy, hetero alkyl, etc; in particular embodiments the alkyl group have $C_{1-6}$, more preferably $C_{1-3}$;
R₂ is substituted or unsubstituted aryl, heteroaryl, or arylcarbonylalkyl;
n is 1-4.

FIG. 16
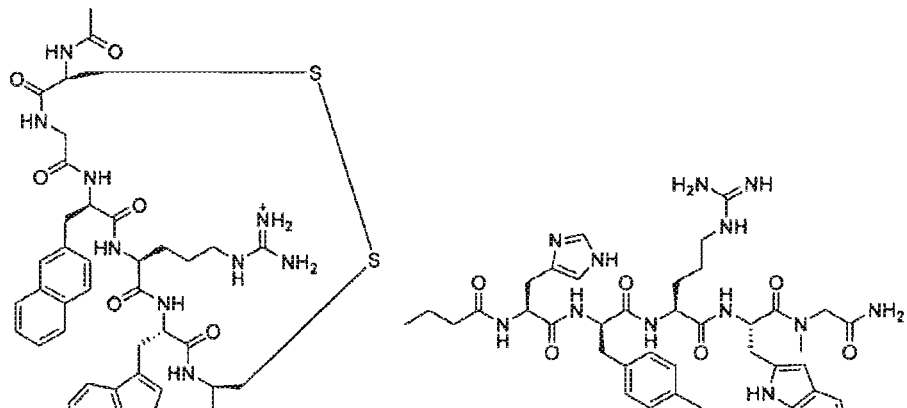
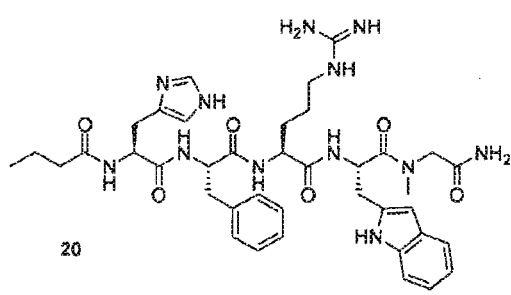
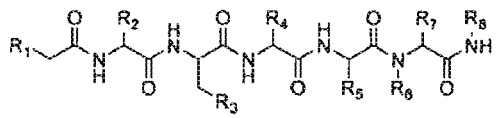
Wherein $R_1$ is alkyl with $C_{1-3}$;
$R_2$ is -S- or H;
$R_3$ is H or [imidazolylmethyl]
$R_4$ is aminoalkyl with the alkyl having $C_{1-5}$, in particular embodiments guanidinoalkyl with the alkyl having $C_{1-5}$, perferably $C_{1-3}$;
$R_5$ is a substituted or unsubstituted aryl or heteroaryl; and
$R_6$ is H, $CH_3$ or $C_1$-$C_3$ alkyl;
$R_7$ is H or -S-
$R_8$ is H, $CH_3$, or $C_{1-3}$ alkyl.

SEQUENCE LISTING

```
<160> NUMBER OF SEQ ID NOS: 18

<210> SEQ ID NO 1
<211> LENGTH: 1000
<212> TYPE: DNA
<213> ORGANISM: Homo sapiens

<400> SEQUENCE: 1
atggtgaact ccacccaccg tgggatgcac acttctctgc acctctggaa ccgcagcagt      60
tacagactgc acagcaatgc cagtgagtcc cttggaaaag gctactctga tggagggtgc     120
tacgagcaac tttttgtctc tcctgaggtg tttgtgactc tgggtgtcat cagcttgttg     180
gagaatatct tagtgattgt ggcaatagcc aagaacaaga atctgcattc acccatgtac     240
tttttcatct gcagcttggc tgtggctgat atgctggtga gcgtttcaaa tggatcagaa     300
accattgtca tcaccctatt aaacagtaca gatacggatg cacagagttt cacagtgaat     360
attgataatg tcattgactc ggtgatctgt agctccttgc ttgcatccat ttgcagcctg     420
ctttcaattg cagtggacag gtactttact atcttctatg ctctccagta ccataacatt     480
atgacagtta agcgggttgg gatcatcata agttgtatct gggcagcttg cacggtttca     540
ggcattttgt tcatcattta ctcagatagt agtgctgtca tcatctgcct catccccatg     600
```

```
ttcttcacca tgctggctct catggcttct ctctatgtcc acatgttcct gatggccagg    660
cttcacatta agaggattgc tgtcctcccc ggcactggtg ccatccgcca aggtgccaat    720
atgaagggag cgattacctt gaccatcctg attggcgtct tgttgtctg ctgggcccca    780 ttcttcctcc acttaatatt ctacatctct tgtcctcaga atccatattg tgtgtgcttc    840
atgtctcact taacttgta tctcatactg atcatgtgta attcaatcat cgatcctctg    900
atttatgcac tccggagtca agaactgagg aaaaccttca agagatcat ctgttgctat    960 cccctgggag gcctttgtga cttgtctagc agatattaaa                        1000
```

<210> SEQ ID NO 2
<211> LENGTH: 332
<212> TYPE: PRT
<213> ORGANISM: Homo sapiens

<400> SEQUENCE: 2

```
Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp Pro Leu Ile Tyr Ala Leu
    290                 295                 300
```

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 3
<211> LENGTH: 999
<212> TYPE: DNA
<213> ORGANISM: Homo sapiens

<400> SEQUENCE: 3

```
atggtgaact ccacccaccg tgggatgcac acttctctgc acctctggaa ccgcagcagt      60
tacagactgc acagcaatgc cagtgagtcc cttggaaaag ctactctga tgagggtgc      120
tacgagcaac tttttgtctc tcctgaggtg tttgtgactc tgggtgtcat cagcttgttg     180
gagaatatct tagtgattgt ggcaatagcc aagaacaaga atctgcattc acccatgtac     240
ttttcatct gcagcttggc tgtggctgat atgctggtga cgtttcaaa tggatcagaa      300
accattatca tcaccctatt aaacagtaca gatacggatg cacagagttt cacagtgaat     360
attgataatg tcattgactc ggtgatctgt agctccttgc ttgcatccat ttgcagcctg     420
ctttcaattg cagtggacag gtactttact atcttctatg ctctccagta ccataacatt     480
atgacagtta agcgggttgg gatcatcata agttgtatct gggcagcttg cacggtttca     540
ggcatttgt tcatcattta ctcagatagt agtgctgtca tcatctgcct catcaccatg     600
ttcttcacca tgctggctct catggcttct ctctatgtcc acatgttcct gatggccagg     660
cttcacatta gaggattgc tgtcctcccc ggcactggtg ccatccgcca aggtgccaat     720
atgaagggag cgattacctt gaccatcctg attggcgtct tgttgtctg ctgggcccca     780
ttcttcctcc acttaatatt ctacatctct tgtcctcaga tccatattg tgtgtgcttc     840
atgtctcact ttaacttgta tctcatactg atcatgtgta attcaatcat cgatcctctg     900
atttatgcac tccggagtca agaactgagg aaaaccttca agagatcat ctgttgctat     960
cccctgggag gcctttgtga cttgtctagc agatattaa                           999
```

<210> SEQ ID NO 4
<211> LENGTH: 332
<212> TYPE: PRT
<213> ORGANISM: Homo sapiens

<400> SEQUENCE: 4

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Ile Ile Thr Leu Leu Asn Ser Thr Asp Thr
            100                 105                 110

Asp Ala Gln Ser Phe Thr Val Asn Ile Asp Asn Val Ile Asp Ser Val 115                 120                 125
Ile Cys Ser Ser Leu Leu Ala Ser Ile Cys Ser Leu Leu Ser Ile Ala
            130                 135                 140
Val Asp Arg Tyr Phe Thr Ile Phe Tyr Ala Leu Gln Tyr His Asn Ile
145                 150                 155                 160
Met Thr Val Lys Arg Val Gly Ile Ile Ser Cys Ile Trp Ala
                165                 170                 175
Cys Thr Val Ser Gly Ile Leu Phe Ile Ile Tyr Ser Asp Ser Ser Ala
            180                 185                 190
Val Ile Ile Cys Leu Ile Thr Met Phe Phe Thr Met Leu Ala Leu Met
            195                 200                 205
Ala Ser Leu Tyr Val His Met Phe Leu Met Ala Arg Leu His Ile Lys
            210                 215                 220
Arg Ile Ala Val Leu Pro Gly Thr Gly Ala Ile Arg Gln Gly Ala Asn
225                 230                 235                 240
Met Lys Gly Ala Ile Thr Leu Thr Ile Leu Ile Gly Val Phe Val Val
                245                 250                 255
Cys Trp Ala Pro Phe Phe Leu His Leu Ile Phe Tyr Ile Ser Cys Pro
            260                 265                 270
Gln Asn Pro Tyr Cys Val Cys Phe Met Ser His Phe Asn Leu Tyr Leu
            275                 280                 285
Ile Leu Ile Met Cys Asn Ser Ile Ile Asp Pro Leu Ile Tyr Ala Leu
            290                 295                 300
Arg Ser Gln Glu Leu Arg Lys Thr Phe Lys Glu Ile Ile Cys Cys Tyr
305                 310                 315                 320
Pro Leu Gly Gly Leu Cys Asp Leu Ser Ser Arg Tyr
                325                 330

<210> SEQ ID NO 5
<211> LENGTH: 1888
<212> TYPE: DNA
<213> ORGANISM: Rattus norvegicus

<400> SEQUENCE: 5
atgctcggga agctcaactt ctgagaggct gcgctgtgag tgtgggcgcg cagatgcaga      60
ggcggctccc agctctccag cgactctcag gaaaaggact ctgaaaagac cccgagtgaa     120
tactacggct aagggaaag ccacaaaaaa cgaactgcag actggtcagc cgagagtgag     180
ctttcagtag cgccagcttc taagaaatg atgagcaaag ctgaacccag aagagaccaa     240
caactccttt gcaagctccg ctgcttctga ccctgttcac cgcaggcgcc aactgcagcc     300
ttccaacttc tacaggcaga caggctggga gaaaaccac tcggggcttc cctgacctag     360
gaggttggac cacttcaagg aggattcgaa tccagctgct gcaggaagat gaactccacc     420
caccaccatg gcatgtatac ttccctccac ctctggaacc gcagcagcca cgggctgcac     480
ggcaatgcca gcgagtctct ggggaagggg cactcagacg gaggatgcta tgagcaactt     540
tttgtctccc ccgaggtgtt tgtgactctg ggtgtcataa gcctgttgga gaacattcta     600
gtgatcgtgg cgatagccaa gaacaagaac ctgcactcac ccatgtactt tttcatctgt     660
agtctggctg tggcggacat gctggtgagc gtttcgaacg ggtcagaaac catcgtcatc     720
accctgctaa acagtacgga cacggacgcc cagagcttca ccgtgaatat tgataatgtc     780
attgactctg tgatctgtag ctccttgctc gcatccattt gcagcctgct ttccattgca     840
gtggacaggt atttcactat cttttacgcg ctccagtacc ataacattat gacggttagg     900

```
cgggtcggga tcatcatcag ttgtatctgg gcagcttgca cagtatcggg cgttcttttt      960
atcatttact cggacagcag cgctgtcatc atctgcctca ttaccatgtt cttcaccatg     1020
ctggttctca tggcctctct ctatgtccac atgttcctga tggcgaggct tcacattaag     1080
aggatcgctg tcctcccggg cacgggtacc atccgacagg gtgccaacat gaagggcgca     1140
attaccttga ccattctgat tggagtgttt gttgtctgct gggccccgtt tttcctccat     1200
ttactgttct acatctcttg tcctcagaat ccatactgcg tgtgcttcat gtctcatttt     1260
aacttgtatc tcatactgat catgtgtaac gctgtcatcg accctctcat ttatgccctg     1320
cggagtcaag aactgaggaa aaccttcaaa gagatcatct gtttctaccc cctgggaggc     1380
atctgtgagt tacctggcag gtattaagtg gggacagagt gcatactagg tagagacctg     1440
cagaatttgt cactcaggca aacctgagc agtgtacttc ccaacagctg cctctactgt      1500
atagtgcttt ggttggaaaa tatctactgt ataaaatgta agtttatgac ttttgacgtg     1560
gggaaaaagt ctcaacgtgt tatgtttatt gaccttactt ttttgtgtg taaactgctt      1620
atttatgttc tacagcgtgg gcgctatgga gttccataaa agaaaaagac acccttatta     1680
aaactttgac agtgtttctt tccatgttat ttatcaagag tcaacccttg ttctttctgt     1740
ggtagcagaa atcagagcct tctgaaaagc tgtttccatt gcatcacccc cacagcacag    1800
cagaagcctg attccactgt ttatggggaa atatttaaac actggatgct cgatcattta    1860
atgagtcagc tctactcgtg aaatttca                                      1888
```

<210> SEQ ID NO 6  
<211> LENGTH: 332  
<212> TYPE: PRT  
<213> ORGANISM: Rattus norvegicus

<400> SEQUENCE: 6

```
Met Asn Ser Thr His His His Gly Met Tyr Thr Ser Leu His Leu Trp
1               5                  10                  15

Asn Arg Ser Ser His Gly Leu His Gly Asn Ala Ser Glu Ser Leu Gly
            20                  25                  30

Lys Gly His Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160

Met Thr Val Arg Arg Val Gly Ile Ile Ile Ser Cys Ile Trp Ala Ala
                165                 170                 175

Cys Thr Val Ser Gly Val Leu Phe Ile Ile Tyr Ser Asp Ser Ser Ala
            180                 185                 190

Val Ile Ile Cys Leu Ile Thr Met Phe Phe Thr Met Leu Val Leu Met
```

|  |  |  | 195 |  |  | 200 |  |  | 205 |  |  |
|---|---|---|---|---|---|---|---|---|---|---|---|

Ala Ser Leu Tyr Val His Met Phe Leu Met Ala Arg Leu His Ile Lys
    210                      215                      220

Arg Ile Ala Val Leu Pro Gly Thr Gly Thr Ile Arg Gln Gly Ala Asn
225                      230                      235                  240

Met Lys Gly Ala Ile Thr Leu Thr Ile Leu Ile Gly Val Phe Val Val
                245                      250                      255

Cys Trp Ala Pro Phe Phe Leu His Leu Leu Phe Tyr Ile Ser Cys Pro
            260                      265                      270

Gln Asn Pro Tyr Cys Val Cys Phe Met Ser His Phe Asn Leu Tyr Leu
        275                      280                  285

Ile Leu Ile Met Cys Asn Ala Val Ile Asp Pro Leu Ile Tyr Ala Leu
        290                  295                  300

Arg Ser Gln Glu Leu Arg Lys Thr Phe Lys Glu Ile Ile Cys Phe Tyr
305                      310                      315                  320

Pro Leu Gly Gly Ile Cys Glu Leu Pro Gly Arg Tyr
                325                      330

<210> SEQ ID NO 7
<211> LENGTH: 2769
<212> TYPE: DNA
<213> ORGANISM: Mus musculus

<400> SEQUENCE: 7

```
gctggctcac aaagatgctc aggaagctga acttctgaga ggctgcggtg tgagtgtggg      60
cgcgcagatg cagacgcggc tcccagcagt acagcgagtc tcagggaaaa ggactctgaa     120
aagaccccga gtgaatacta agtgaaagc cgcactgaga gagagagaaa aaaaagcaaa     180
cagcagactg tcaaccgag aatgagcatt cagaagcacc agcttctaaa gagacgatga     240
tctgagccga acccagaaga gaccaacaac tcctttgcga gttccgctgc ttctgaccct     300
gctcctagca ggcgccaagc gcagcctccc aacttctaca ggcatacaga ctgggagaga     360
atcactcgga gcttccctga cccaggaggt tggatcagtt caaggaggac tcaaatccag     420
ctgctgcagg aagatgaact ccacccacca ccatggcatg tatacttccc tccacctctg     480
gaaccgcagc agctacgggc tgcacggcaa tgccagcgag tcgctgggga agggccaccc     540
ggacggagga tgctatgagc aacttttgt ttcccccgag gtgtttgtga ctctgggtgt     600
cataagcctg ttggagaaca ttctagtgat cgtggcgata gccaagaaca agaacctgca     660
ctcacccatg tactttttca tctgtagcct ggctgtggca gatatgctgg tgagcgtttc     720
gaatgggtcg gaaaccatcg tcattaccct gttaaacagt acggatacgg atgcccagag     780
cttcaccgtg aacattgata atgtcattga ctctgtgatc tgtagctcct tgctcgcatc     840
catttgcagc ctgctttcca ttgcggtgga caggtatttc actatctttt acgcgctcca     900
gtaccataac atcatgacgg ttaggcgggt cgggatcatc ataagttgta tctgggcagc     960
ttgcactgtg tcaggcgtcc tcttcatcat ttactcggac agcagcgctg tcatcatctg    1020
cctcatttcc atgttcttca ctatgctagt tctcatggcc tctctctatg tccacatgtt    1080
cctgatggcg aggcttcaca ttaagaggat tgctgtcctc ccaggcacag ggaccatccg    1140
ccagggtacc aacatgaagg gggcgattac cttgaccatc ctgattggag tctttgttgt    1200
ctgctgggcc ccgttctttc tccatttact gttctacatc tcttgccctc agaatccata    1260
ctgcgtgtgc ttcatgtctc attttaattt gtatctcata ctgatcatgt gtaacgccgt    1320
catcgaccct ctcatttatg ccctccggag tcaagaactg aggaaaactt tcaaagagat    1380
```

```
catctgtttc tatcctctgg gaggcatctg tgagttgtct agcaggtatt aagtggggga    1440
cagagtgcaa actaggtaga tacctgcaga ctttgtcact ctggcccgat ctgagcagtg    1500
tacttcccaa cagctgcctc ttctgtgtaa tgctttggtt gaaatatct actgtataaa     1560 tgtaagtttg tgacttttga catggaaaaa aaagtctcaa cgtgttatgt ttattgacac    1620 gctattttt ttgtttgtaa aatgcttatt tatgttctat atagtgtggg cgttatgaat     1680
tgacatgaaa gaaaaacaga caccctatt aaaactttga cagtgtttct ttcctgttat     1740
ttatcaaggt tccacacttg ttctttctgt agtggccgaa atcagaacct tattaaacgt    1800
gttctcagct gttctcatgt attagcccca cagtactgca gaggcactga ccccactgtt    1860
tatggggaaa tatttaaaca ctacatgctt gatcattaaa atgagtcagc tctcttagtg    1920
aaatttcgag caatcgaata aaagcttgcc tattatcctt gctgtccaaa tacactgatg    1980 cttctttta agtaaaggaa agagaaaggg ggaagaagca gctactgagg agaaagtgag     2040
atttctgtca catgcatttc tccaagaagg aatggttcat tgcccgagac tcagagttca    2100
cacaggcaag tcagctgtgg taggggaaat gcccacttaa tagattaaag atattataat    2160
agataataat agataaaata gattaataga taaaatagat accaatctta atagattaaa    2220
gtgtcctgtt aaatataaac tgtccacacc atgctgaaat ttcctatgcc aaatgatacc    2280
ccaccataac agaatgattt ctttctggct tcttaccagg gatctggttc ctacagaaag    2340
gtctagaaca gctccctctg cacttagagg tccagcgttc atttcatctt agagttaata    2400
gtgagttgtg ctatctttca tgtggcgggg gacttgttgt tcactttctg attacttttt    2460
gagctggaat ataagtgctg aagatcaagt gatttaattc ccaagccaaa tccacatcac    2520
aaaacatttt gggacagggt ttgtaaatat ctaaagtgtg gagccctgtg gtgcttgcac    2580
ataacgagat ggaaagagaa cacaaatggg gtcctggaag gtacagtaaa acaccctgct    2640
gttcttagtc atgtcttggg atggggaatg cttgttttct ccaaactaat accaaaggtg    2700
tggccactga gcaaccaaat ctatgctttc tagtctgtgt atactttgaa ataaaaggga    2760
taaaaacct                                                           2769
```

<210> SEQ ID NO 8
<211> LENGTH: 332
<212> TYPE: PRT
<213> ORGANISM: Mus musculus

<400> SEQUENCE: 8

```
Met Asn Ser Thr His His His Gly Met Tyr Thr Ser Leu His Leu Trp
 1               5                   10                  15

Asn Arg Ser Ser Tyr Gly Leu His Ser Asn Ala Ser Glu Ser Leu Gly
            20                  25                  30

Lys Gly His Pro Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
```

```
                 115                 120                 125
Ile Cys Ser Ser Leu Leu Ala Ser Ile Cys Ser Leu Leu Ser Ile Ala
        130                 135                 140

Val Asp Arg Tyr Phe Thr Ile Phe Tyr Ala Leu Gln Tyr His Asn Ile
145                 150                 155                 160

Met Thr Val Arg Arg Val Gly Ile Ile Ser Cys Ile Trp Ala Ala
                165                 170                 175

Cys Thr Val Ser Gly Val Leu Phe Ile Ile Tyr Ser Asp Ser Ser Ala
                180                 185                 190

Val Ile Ile Cys Leu Ile Ser Met Phe Phe Thr Met Leu Val Leu Met
            195                 200                 205

Ala Ser Leu Tyr Val His Met Phe Leu Met Ala Arg Leu His Ile Lys
        210                 215                 220

Arg Ile Ala Val Leu Pro Gly Thr Gly Thr Ile Arg Gln Gly Thr Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Leu Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ala Val Ile Asp Pro Leu Ile Tyr Ala Leu
    290                 295                 300

Arg Ser Gln Glu Leu Arg Lys Thr Phe Lys Glu Ile Ile Cys Phe Tyr
305                 310                 315                 320

Pro Leu Gly Gly Ile Cys Glu Leu Ser Ser Arg Tyr
                325                 330

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MOD_RES
<222> LOCATION: (7)..(7)
<223> OTHER INFORMATION: AMIDATION

<400> SEQUENCE: 9

Xaa Gly Lys Phe Arg Trp Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: MISC_FEATURE
```

```
<222> LOCATION: (4)..(4)
<223> OTHER INFORMATION: beta-naphthylalanine (2)
<220> FEATURE:
<221> NAME/KEY: MOD_RES
<222> LOCATION: (4)..(4)
<223> OTHER INFORMATION: AMIDATION

<400> SEQUENCE: 10

Xaa Gly Lys Xaa Arg Trp Gly
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide, cyclic
<220> FEATURE:
<221> NAME/KEY: MOD_RES
<222> LOCATION: (1)..(4)
<223> OTHER INFORMATION: ACETYLATION, Nle
<220> FEATURE:
<221> NAME/KEY: MOD_RES
<222> LOCATION: (2)..(4)
<223> OTHER INFORMATION: Nle
<220> FEATURE:
<221> NAME/KEY: MISC_FEATURE
<222> LOCATION: (7)..(7)
<223> OTHER INFORMATION: beta-naphthylalanine (2')
<220> FEATURE:
<221> NAME/KEY: MOD_RES
<222> LOCATION: (10)..(10)
<223> OTHER INFORMATION: AMIDATION

<400> SEQUENCE: 11

Xaa Xaa Xaa Xaa Asp His Xaa Arg Trp Lys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: D-(2') beta-naphthylalanine
<220> FEATURE:
<221> NAME/KEY: MOD_RES
<222> LOCATION: (12)..(12)
<223> OTHER INFORMATION: AMIDATION

<400> SEQUENCE: 12

Cys Glu His Xaa Arg Trp Gly Cys Pro Pro Lys Asp
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

```
<222> LOCATION: (2)..(2)
<223> OTHER INFORMATION: Nle
<220> FEATURE:
<221> NAME/KEY: MISC_FEATURE
<222> LOCATION: (5)..(5)
<223> OTHER INFORMATION: D-(2') beta-naphthylalanine
<220> FEATURE:
<221> NAME/KEY: MOD_RES
<222> LOCATION: (9)..(9)
<223> OTHER INFORMATION: AMIDATION

<400> SEQUENCE: 13

Cys Xaa Arg His Xaa Arg Trp Gly Cys
1               5

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: D-Phe (3,4-di-Cl)
<220> FEATURE:
<221> NAME/KEY: MOD_RES
<222> LOCATION: (12)..(12)
<223> OTHER INFORMATION: AMIDATION

<400> SEQUENCE: 14

Cys Glu His Phe Arg Trp Gly Cys Pro Pro Lys Asp
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide, cyclic
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: MISC_FEATURE
<222> LOCATION: (2)..(2)
<223> OTHER INFORMATION: c [Asp
<220> FEATURE:
<221> NAME/KEY: MISC_FEATURE
<222> LOCATION: (3)..(3)
<223> OTHER INFORMATION: Che
<220> FEATURE:
<221> NAME/KEY: MISC_FEATURE
<222> LOCATION: (4)..(4)
<223> OTHER INFORMATION: DNal(2')
<220> FEATURE:
<221> NAME/KEY: MOD_RES
<222> LOCATION: (7)..(7)
<223> OTHER INFORMATION: AMIDATION

<400> SEQUENCE: 15

Xaa Asp Xaa Xaa Arg Trp Lys
1               5

<210> SEQ ID NO 16
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: MISC_FEATURE
<222> LOCATION: (2)..(2)
<223> OTHER INFORMATION: c[Asp
<220> FEATURE:
<221> NAME/KEY: MISC_FEATURE
<222> LOCATION: (3)..(3)
<223> OTHER INFORMATION: Cpe
<220> FEATURE:
<221> NAME/KEY: MISC_FEATURE
<222> LOCATION: (4)..(4)
<223> OTHER INFORMATION: DNal (2')
<220> FEATURE:
<221> NAME/KEY: MOD_RES
<222> LOCATION: (7)..(7)
<223> OTHER INFORMATION: AMIDATION

<400> SEQUENCE: 16

Xaa Asp Xaa Xaa Arg Trp Lys
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic petide
<220> FEATURE:
<221> NAME/KEY: MOD_RES
<222> LOCATION: (1)..(1)
<223> OTHER INFORMATION: BLOCKED, cyclo (1,6) - suc
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MOD_RES
<222> LOCATION: (5)..(5)
<223> OTHER INFORMATION: AMIDATION

<400> SEQUENCE: 17

His Phe Arg Trp Lys
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION, DArg
<220> FEATURE:
<221> NAME/KEY: MISC_FEATURE
<222> LOCATION: (5)..(5)
<223> OTHER INFORMATION: D amino acid
<220> FEATURE:
<221> NAME/KEY: MOD_RES
<222> LOCATION: (8)..(8)
<223> OTHER INFORMATION: AMIDATION

<400> SEQUENCE: 18

Arg Cys Glu His Phe Arg Trp Cys
1               5
```

PHARMACOLOGICAL CHAPERONES FOR TREATING OBESITY

CROSS-REFERENCE TO RELATED APPLICATIONS

This application is a continuation of U.S. Ser. No. 11/446,429 filed Jun. 2, 2006 which claims priority form U.S. Provisional Patent Application Nos. 60/687,648 filed Jun. 3, 2005, and 60/799,968 filed May 12, 2006, each of which is incorporated by reference herein in its entirety.

FIELD OF THE INVENTION

The invention relates to methods of enhancing normal melanocortin-4 receptor (MC4R) activity, and to enhancing activity of an MC4R having a mutation or mutations which affects protein folding and/or processing of the MC4R. The invention provides a method of treating an individual having a condition in which increased activity of an MC4R at the cell surface would be beneficial, such as in obesity, by administering an effective amount of a pharmacological chaperone for the MC4R. The invention provides MC4R pharmacological chaperones which enhance activity of MC4R. The invention further provides a method of screening to identify pharmacological chaperones which enhance folding of an MC4R in the endoplasmic reticulum (ER), in order to enhance activity of the MC4R at the cell surface.

BACKGROUND OF THE INVENTION

Obesity

Obesity represents the most prevalent of body weight disorders, and it is the most important nutritional disorder in the Western world, with estimates of its prevalence ranging from 30% to 50% of the middle-aged population. The number of overweight and obese Americans has continued to increase since 1960, a trend that is not slowing down. Today, 64.5 percent of adult Americans (about 127 million) are categorized as being overweight or obese. Each year, obesity causes at least 300,000 deaths in the U.S., and healthcare costs of American adults with obesity amount to approximately $100 billion (American Obesity Association).

Obesity increases an individual's risk of developing conditions such as high blood pressure, diabetes (type 2), hyperlipidemia, heart disease, hypertension, stroke, gallbladder disease, and cancer of the breast, prostate, and colon (see, e.g., Nishina, P. M. et al., 1994, Metab. 43: 554-558; Grundy, S. M. & Barnett, J. P., 1990, Dis. Mon. 36; 641-731). In the U.S., the incidence of being overweight or obese occurs at higher rates in racial/ethnic minority populations such as African American and Hispanic Americans, compared with Caucasian Americans. Women and persons of low socioeconomic status within minority populations appear to particularly be affected by excess weight and obesity. This trend is not limited to adults. Approximately 30.3 percent of children (ages 6 to 11) are overweight and 15.3 percent are obese. For adolescents (ages 12 to 19), 30.4 percent are overweight and 15.5 percent are obese. Diabetes, hypertension and other obesity-related chronic diseases that are prevalent among adults have now become more common in children and young adults. Poor dietary habits and inactivity are reported to contribute to the increase of obesity in youth.

Additionally, risk factors for developing childhood obesity include having overweight parents, or parents unconcerned about their child's weight, increased energy intake due to larger serving sizes, increased sedentary lifestyle and decreased transport-related activity (walking to school or to the bus stop), having a temperament with high levels of anger/frustration (which may cause parents to give their child extra food and calories to decrease tantrums); having Down's Syndrome, mother's pregnancy Body Mass Index (BMI) and first born status (increased prevalence of obesity).

One tool used for diagnosing obesity in adults is calculating an individual's BMI, which is a measure of body weight for height (Garrow and Webster, *International Journal of Obesity* 1985; 9:147-153). A BMI of 25 to 29.9 indicates that an individual is overweight, while a BMI of 30 or above is indicative of obesity. For children, BMI is gender and age specific (Pietrobelli et al., *Journal of Pediatrics* 1998; 132: 204-210).

Risk factors for developing obesity in adulthood include poor diet (high-calorie, low nutrients); lack of physical activity; working varied shifts; quitting smoking, having certain medical conditions such as rare hereditary diseases, and hormonal imbalances (such as hypothyroid, Cushing's disease and polycystic ovarian syndrome); certain medications (steroids and some antidepressants); being a racial or ethnic minority (especially a female minority); low socioeconomic status; age (increased risk from 20-55), pregnancy; and retirement (due to altered schedule).

Melanocortin 4 Receptor and Obesity

The melanocortin 4 receptor (MC4R) has been implicated in the regulation of body weight (Graham et al, *Nat. Genetics* 1997; 17: 273-4). MC4R is expressed in the brain, including the hypothalamus, which influences food intake. Numerous mutations affecting MC4R activity have been found and many are associated with obesity including early-onset (childhood) obesity (Nijenhuis et al., *J. Biol. Chem.* 2003, 278:22939-45; Branson et al., *New Eng. J. Med.* 2003, 348: 1096-1103; Gu et al., *Diabetes* 1999, 48:635-39; Farooqi et al., *New Eng. J. Med.* 2003, 348: 1085-95; Tao et al., *Endocrinology* 2003, 144:4544-51).

Current Treatments

Current anti-obesity drugs have limited efficacy and numerous side effects (Crowley, V. E., Yeo, G. S. & O'Rahilly, S., *Nat. Rev. Drug Discov.* 2002; 1, 276-86). With obesity reaching epidemic proportions worldwide, there is a pressing need for the development of adequate therapeutics in this area. In recent years, hormones and neuropeptides involved in the regulation of appetite, body energy expenditures and fat mass accumulation have emerged as potential anti-obesity drugs (McMinn, J. E., Baskin, D. G. & Schwartz, M. W., *Obes Rev* 2000; 1:37-46; Drazen, D. L. & Woods, S. C., *Curr Opin Clin Nutr Metab Care* 2003; 6:621-629). At present, however, these peptides require parenteral administration. The prospect of daily injections to control obesity for extended periods of time (since obesity is a chronic condition) is not very encouraging and limits the use of these drugs.

Molecular Chaperones Stabilize Proper Protein Folding

Proteins are synthesized in the cytoplasm, and the newly synthesized proteins are secreted into the lumen of the endoplasmic reticulum (ER) in a largely unfolded state. In general, protein folding is governed by the principle of self assembly. Newly synthesized polypeptides fold into their native conformation based on their amino acid sequences (Anfinsen et al., Adv. Protein Chem. 1975; 29:205-300). In vivo, protein folding is complicated, because the combination of ambient temperature and high protein concentration stimulates the process of aggregation, in which amino acids normally buried in the hydrophobic core interact with their neighbors non-specifically. To avoid this problem, protein folding is usually facilitated by a special group of proteins called chaperones, which prevent nascent polypeptide chains from aggregating by binding to unfolded protein such that the protein refolds in the native conformation (Hartl, *Nature* 1996; 381:571-580).

Endogenous molecular chaperones are present in virtually all types of cells and in most cellular compartments. Some are involved in the transport of proteins and permit cells to survive under stresses such as heat shock and glucose starvation (Gething et al., *Nature* 1992; 355:33-45; Caplan, *Trends Cell. Biol.* 1999; 9:262-268; Lin et al., *Mol. Biol. Cell.* 1993; 4:109-1119; Bergeron et al., *Trends Biochem. Sci.* 1994; 19:124-128). Among the endogenous chaperones, BiP (immunoglobulin heavy-chain binding protein, Grp78) is the best characterized chaperone of the ER (Haas, *Curr. Top. Microbiol. Immunol.* 1991; 167:71-82). Like other chaperones, BiP interacts with many secretory and membrane proteins within the ER throughout their maturation. When nascent protein folding proceeds smoothly, this interaction is normally weak and short-lived. Once the native protein conformation, is achieved, the molecular chaperone no longer interacts with the protein. BiP binding to a protein that fails to fold, assemble, or be properly glycosylated becomes stable, and usually leads to degradation of the protein through the ER-associated degradation pathway. This process serves as a "quality control" system in the ER, ensuring that only those properly folded and assembled proteins are transported out of the ER for further maturation, and improperly folded proteins are retained for subsequent degradation (Hurtley et al., *Annu. Rev. Cell. Biol.* 1989; 5:277-307). Due to the combined actions of the inefficiency of the thermodynamic protein folding process and the ER quality control system, only a fraction of nascent (non-mutated) proteins become folded into a functional conformation and successfully exit the ER.

Pharmacological Chaperones Derived from Specific Enzyme Inhibitors Rescue Mutant Enzymes and Enhance Wild-Type Enzymes It has previously been shown that small molecule inhibitors of enzymes associated with lysosomal storage disorders (LSDs) can both rescue folding and activity of the mutant enzyme, and enhance folding and activity of the wild-type enzyme (see U.S. Pat. Nos. 6,274,597; 6,583,158; 6,589,964; 6,599,919; and 6,916,829, all incorporated herein by reference). In particular, it was discovered that administration of small molecule derivatives of glucose and galactose, which were specific competitive inhibitors of mutant enzymes associated with LSDs, effectively increased in vitro and in vivo stability of the mutant enzymes and enhanced the mutant enzyme activity. The original theory behind this strategy is as follows: since the mutant enzyme protein folds improperly in the ER (Ishii et al., *Biochem. Biophys. Res. Comm.* 1996, 220: 812-815), the enzyme protein is retarded in the normal transport pathway (ER→Golgi apparatus→endosome→lysosome) and rapidly degraded. Therefore, a compound which stabilizes the correct folding of a mutant protein will serve as an active site-specific chaperone for the mutant protein to promote its smooth escape from the ER quality control system. Enzyme inhibitors occupy the catalytic center, resulting in stabilization of enzyme conformation in cells in culture and in animals. These specific chaperones were designated "active site-specific chaperones (ASSCs)" since they bound in the active site of the enzyme.

In addition to rescuing the mutant enzymes, the ASSCs enhance ER secretion and activity of recombinant wild-type enzymes. An ASSC facilitates folding of overexpressed wild-type enzyme, which is otherwise retarded in the ER quality control system because overexpression and over production of the enzyme exceeds the capacity of the ER and leads to protein aggregation and degradation. Thus, a compound that induces a stable molecular conformation of an enzyme during folding serves as a "chaperone" to stabilize the enzyme in a proper conformation for exit from the ER. As noted above, for enzymes, one such compound unexpectedly turned out to be a competitive inhibitor of the enzyme.

Enhancement of Other Proteins with Chaperones

In addition to the LSDs, a large and diverse number of diseases are now recognized as "conformational diseases" that are caused by adoption of non-native protein conformations, which may lead to retardation of the protein in the ER and ultimate degradation of the proteins (Kuznetsov et al., *N. Engl. J. Med.* 1998; 339:1688-1695; Thomas et al., *Trends Biochem. Sci.* 1995, 20:456-459; Bychkova et al., *FEBS Lett.* 1995; 359:6-8; Brooks, *FEBS Lett.* 1997; 409:115-120).

For example, small synthetic compounds were found to stabilize the DNA binding domain of mutant forms of the tumor suppressor protein p53, thereby allowing the protein to maintain an active conformation (Foster et al., *Science* 1999; 286:2507-10). Synthesis of receptors has been shove to be rescued by small molecule receptor antagonists and ligands (Morello et al., *J. Clin. Invest.* 2000; 105: 887-95; Petaja-Repo et al., *EMBO J.* 2002; 21:1628-37). Even pharmacological rescue of membrane channel proteins and other plasma membrane transporters has been demonstrated using channel-blocking drugs or substrates (Rajamani et al., *Circulation* 2002; 105:2830-5; Zhou et al., *J. Biol. Chem.* 1999; 274:31123-26; Loo et al., *J. Biol. Chem.* 1997; 272: 709-12; Pedemonte et al., *J. Clin. Inves.* 2005; 115: 2564-71).

There remains in the art a particular need to address deficiencies in MC4R protein function which are both related and unrelated to MC4R mutation.

SUMMARY OF THE INVENTION

As described herein, the present invention provides a method for enhancing the activity of the melanocortin-4 receptor (MC4R), e.g., for the treatment of obesity, in subjects who have a folding mutation in the gene encoding MC4R, or in subjects for whom an increase in wild-type MC4R activity would be beneficial.

In one embodiment, the present invention provides a method for enhancing intracellular folding of an MC4R polypeptide into a functional conformation by contacting an MC4R-expressing cell with an effective amount of a pharmacological chaperone. Enhancing intracellular folding of MC4R, resulting in enhanced expression on the cell surface of, e.g., neurons of the hypothalamus, reduces the urge to eat, and, therefore, is useful in the treatment of overeating disorders, such as binge-eating.

In one embodiment, the MC4R polypeptide is a wild-type MC4R polypeptide, which, for example, has a sequence as depicted in SEQ ID NO: 2, SEQ ID NO: 4, SEQ ID NO: 6, or SEQ ID NO: 8.

In another embodiment, the MC4R polypeptide is a mutant MC4R polypeptide. In this embodiment, the mutant polypeptide contains one or more mutations that result in reduced or improper intracellular folding of the MC4R polypeptide. Exemplary mutations are as follows: P78L, R165Q, R165W, I125K, C271Y, T11A, A175T, I316L, I316S, I317T, N97D, G98R, N62S, C271R, S58C, N62S, N97D, Y157S, I102S, L106P, L250Q, Y287X, P299H, S58C, CTCT at codon 211, and TGAT insertion at codon 244.

In one embodiment, the pharmacological chaperone is an MC4R antagonist. In another embodiment, the pharmacological chaperone is an MC4R agonist. In other embodiments, the pharmacological chaperone is an MC4R partial agonist and/or inverse agonist.

The present invention also provides a method for enhancing cell surface expression of an MC4R polypeptide. This method comprises contacting an MC4R-expressing cell with an effective amount of a pharmacological chaperone. This embodiment of the invention pertains to both wild-type MC4R polypeptides and mutant MC4R polypeptides, and the pharmacological chaperones set forth above, for methods of enhancing intracellular folding of MC4R polypeptides.

The present invention also provides a screening method for identifying a chaperone for an MC4R polypeptide by contacting a test compound to a reaction mixture that comprises a cell expressing an MC4R polypeptide; detecting stability, activity, and/or cell surface localization of the MC4R polypeptide in the reaction mixture in the presence of the test compound; and comparing stability, activity, and/or cell surface localization of the MC4R polypeptide in the presence of the test compound to the stability, activity, and/or cell surface localization of the MC4R polypeptide in the absence of said test compound, where detection of increased stability, activity, and/or cell surface localization in the presence of the test compound relative to the absence of the test compound indicates that the test compound is a chaperone for the MC4R polypeptide.

In one embodiment of this screening method, the MC4R polypeptide comprises an amino acid sequence selected from, the group consisting of SEQ ID NOs: 2, 4, 6 and 8.

In another embodiment of this screening method, the MC4R polypeptide comprises a mutation associated with misfolding of the MC4R polypeptide. In specific embodiments, the misfolding mutation is one or more of the following alterations: P78L, R165Q or R165W, I125K, C271Y, T11A, A175T, I316L, I316S, I317T, N97D, G98R, N62S, C271R, S58C, N62S, N97D, Y157S, I102S, L106P, L250Q, Y287X, P299H, S58C, CTCT at codon 211, or TGAT insertion at codon 244.

In one embodiment, the reaction mixture is cell-based. In another embodiment, the reaction mixture is cell-free.

In one embodiment, the screening method further includes detecting activity of an MC4R polypeptide, e.g., on the cell surface. In another embodiment, the activity is measured through cAMP activation.

The present invention will be further understood by reference to the Detailed Description and the Examples.

BRIEF DESCRIPTION OF THE DRAWINGS

FIG. 14. Structure of compound class based upon compounds 3, 9, 10, 11, and 21.

FIG. 15. Structure of compound class based upon compounds 4, 8, 24, and 25.

FIG. 16. Structure of compound class based upon compounds 18-20.

DETAILED DESCRIPTION

The present invention relates to the discovery that small molecules can be identified to rescue protein folding and processing of mutant and wild-type MC4R polypeptides and enhance protein stability on the cell surface of neurons, which in turn, decreases hunger and overeating. The pharmacological chaperones bind specifically to the MC4R protein and induce or stabilize a functional conformation of the mutant or wild-type MC4R. The invention therefore permits specific rescue of mutant MC4R, as well as enhanced expression of wild-type MC4R at the cell surface. Accordingly, pharmacological chaperones for MC4R can be used for the treatment of disorders where rescue of, or increased stability or activity of, MC4R is desired, e.g., the condition of being overweight or obese.

The invention is based, in part, on the discovery that administration of a pharmacological chaperone to a human resulted in a meaningful increase in the level of activity of a wild-type protein. This discovery, combined with an understanding of a pharmacological chaperone's ability to promote proper protein folding in the ER, leading to correct protein trafficking and significantly increased protein activity, advantageously provides the ability to achieve sufficient protein activity to reverse or ameliorate a disease, disorder, or condition, particularly in a human subject. This phenomenon is highly specific to the protein specifically bound by the particular pharmacological chaperone, in contrast to methods using compounds that operate generally to increase expression of all proteins, called "chemical chaperones."

Figure 12:
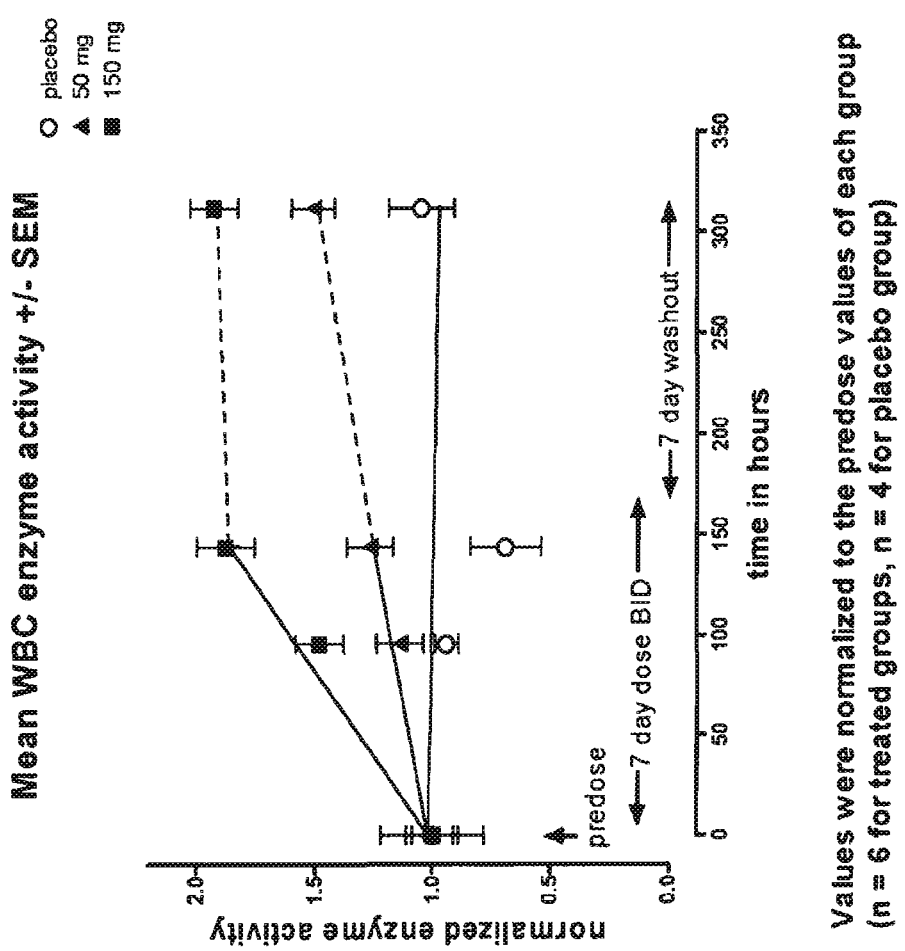
FIG. 12. Mean α-galactosidase A activity in white blood cells from normal, healthy volunteers who received 50 mg 1-deoxygalactonojirimycin (DGJ) b.i.d. (triangles), 150 mg DGJ b.i.d. (squares), or placebo (open circles).
Figure 13:
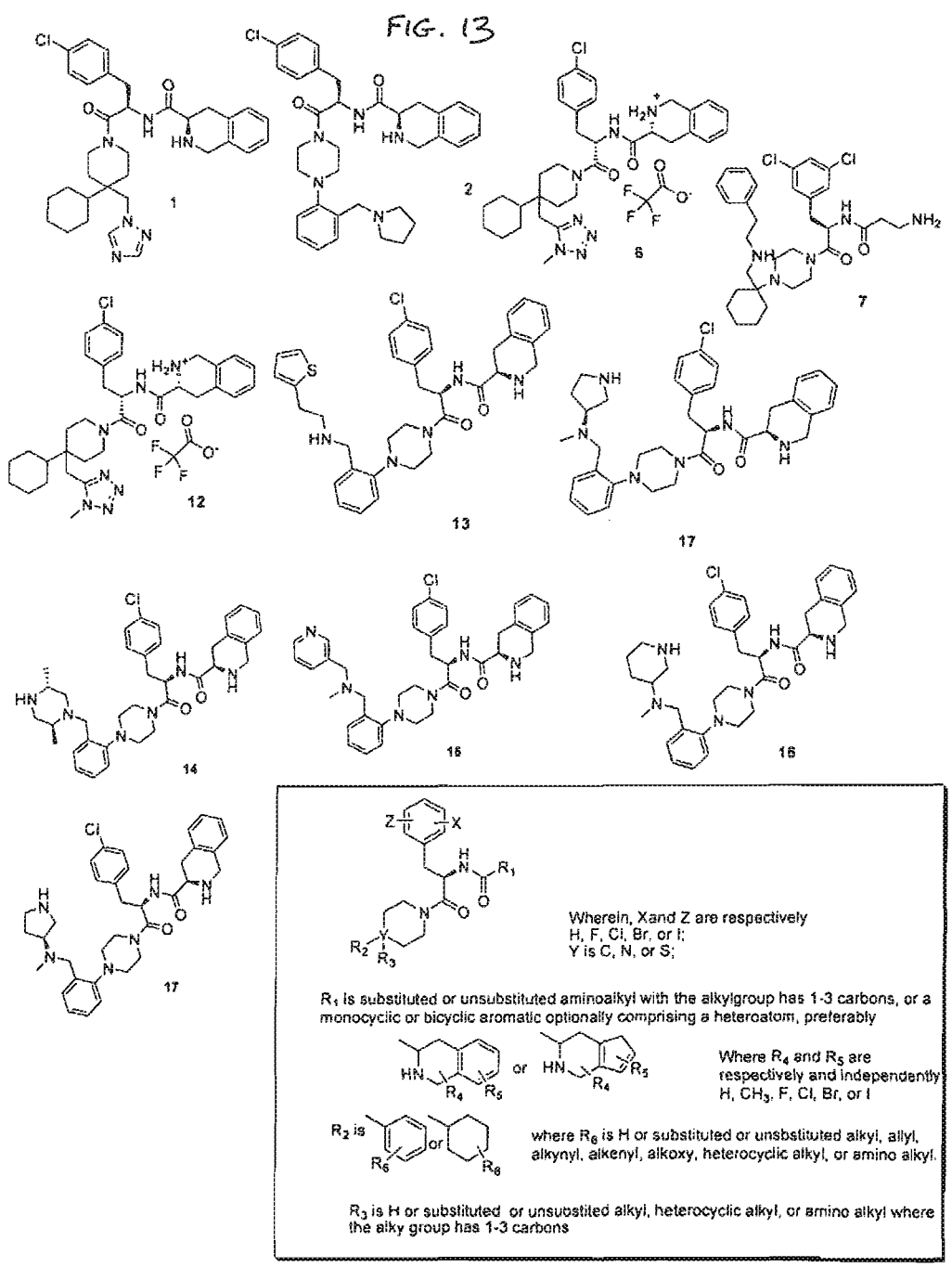
FIG. 13. Structure of compound class based upon compounds 1, 2, 6, 7, and 12-17.

Certain experimental results underlie the present invention: pharmacological chaperones increased endogenous wild-type protein activity in humans to about 120% of normal, 130% of normal, and 145% of normal at a lower dose, and to 150% and 185% of normal at a higher dose after administration of a pharmacological chaperone (see Example 7 and FIG. 12). This level of increase in vivo was not predictable from results with cells in tissue culture which remain exposed to the pharmacological chaperone. For example, U.S. Pat. No. 6,274,597 describes a 30% increase of α-galactosidase A (α-Gal A) activity in normal lymphoblasts cultured in vitro with deoxygalactonojirimycin (DGJ), a pharmacological chaperone. Given the expectation that physiological clearance processes would be expected to reduce the effects of pharmacological chaperones on normal proteins in vivo, it was not expected that a pharmacological chaperone would yield a significant increase in wild-type protein activity. Example 10 of U.S. Pat. No. 6,274,597 describes an increase in activity of a mutant enzyme in transgenic mice treated for one week with a pharmacological chaperone. However, these experiments involved mutant forms of the rescued protein, not wild-type, and were conducted in mice, so the results were not predictive or suggestive of the results observed for wild-type protein in humans.

There was no basis to expect that a pharmacological chaperone could increase the level of activity of a wild-type protein in vivo by at least 20-25%, i.e., by at least 1.2-fold or 120% of normal, or by 30% (1.3-fold, 130% of normal), 40% (1.4-fold, 140% of normal), and particularly not by at least about 50% (1.5-fold, 150% of normal). Yet, as exemplified herein, administration of DGJ to subjects resulted in a dose-dependent increase in α-Gal A. This extraordinary effect results from titrating the pharmacological chaperone, which is already demonstrated in accordance with existing technology to rescue a mutant form of the protein, to achieve the disclosed increase in activity or wild-type protein. Accordingly, the invention provides for titrating a dose of a pharmacological chaperone that has been found to rescue activity of a mutant protein to increase the level of activity of a wild-type protein by a defined amount.

DEFINITIONS

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the term "pharmacological chaperone," or sometimes "specific pharmacological chaperone" ("SPC"), refers to a molecule that specifically binds to MC4R and has one or more of the following effects: (i) enhancing the formation of a stable molecular conformation of the protein; (ii) enhances proper trafficking of the protein from the ER to another cellular location, preferably a native cellular location, i.e., preventing ER-associated degradation of the protein; (iii) preventing aggregation of conformationally unstable, i.e., misfolded proteins; (iv) restoring or enhancing at least partial wild-type function, stability, and/or activity of the protein; and/or (v) improving the phenotype or function of the cell harboring MC4R. Thus, a pharmacological chaperone for MC4R is a molecule that binds to MC4R, resulting in proper folding, trafficking, non-aggregation, and activity of MC4R. As used herein, this term does not refer to endogenous chaperones, such as BiP, or to non-specific agents which have demonstrated non-specific chaperone activity against various proteins, such as glycerol, DMSO or deuterated water, i.e., chemical chaperones (see Welch et al., *Cell Stress and Chaperones* 1996; 1(2):109-115; Welch et al., *Journal of Bioenergetics and Biomembranes* 1997; 29(5):491-502; U.S. Pat. No. 5,900,360; U.S. Pat. No. 6,270,954; and U.S. Pat. No. 6,541,195). It includes specific binding molecules, e.g. specific pharmacological chaperones (discussed above), inhibitors or antagonists, and agonists.

As used herein, the term "specifically binds" refers to the interaction of a pharmacological chaperone with MC4R, specifically, an interaction with amino acid residues of MC4R that directly participate in contacting the pharmacological chaperone. A pharmacological chaperone specifically binds to a target protein, here MC4R, to exert a chaperone effect on MC4R, and not on a generic group of related or unrelated proteins. The amino acid residues of MC4R that interact with any given MC4R pharmacological chaperone may or may not be within the MC4R ligand-binding domain, i.e. the domain that binds the natural ligand MSH, or any other MC4R "active site," e.g., the G-protein binding domain. Specific binding can be evaluated through routine binding assays or through structural studies, e.g., co-crystallization, NMR, and the like. Examples of amino acids in the MSH ligand-binding domain of MC4R include but are not limited to Phe284 and Tyr268 (using, e.g., SEQ ID NO: 2 as a reference sequence).

In one non-limiting embodiment, the pharmacological chaperone is an inhibitor or antagonist of MC4R. In another non-limiting embodiment, the pharmacological chaperone is an agonist of MC4R. In yet another embodiment, the pharmacological chaperone is a mixed agonist/antagonist. As used herein, the term "antagonist" refers to any molecule that binds to a protein and either partially or completely blocks, inhibits, reduces, or neutralizes an activity of MC4R. The term "agonist" refers to any molecule that binds to a protein and at least partially increases, enhances, restores, or mimics an activity of MC4R. As discussed below, such molecules are known for MC4R.

As used herein, the terms "enhance MC4R conformational stability" or "increase MC4R conformational stability" refer to increasing the amount or proportion of MC4R that adopts a functional conformation in a cell contacted with a pharmacological chaperone specific for MC4R, relative to MC4R in a cell (preferably of the same cell-type or the same cell, e.g., at an earlier time) not contacted with the pharmacological chaperone specific for MC4R. In one embodiment, the cells do not express a conformation mutant MC4R. In another embodiment, the cells do express a mutant MC4R polynucleotide encoding a polypeptide e.g., a conformational mutant MC4R.

As used herein, the terms "enhance MC4R trafficking" or "increase MC4R trafficking" refer to increasing the efficiency of transport of MC4R to the plasma membrane in a cell contacted with a pharmacological chaperone specific for MC4R, relative to the efficiency of transport of MC4R in a cell (preferably of the same cell-type or the same cell, e.g., at an earlier time) not contacted with the pharmacological chaperone specific for MC4R.

As used herein, the terms "enhance MC4R activity" or "increase MC4R activity" refer to increasing the activity of MC4R, as described herein, in a cell contacted with a pharmacological chaperone specific for MC4R, relative to the activity of MC4R in a cell (preferably of the same cell-type or the same cell, e.g., at an earlier time) not contacted with the pharmacological chaperone specific for MC4R.

As used herein, the terms "enhance MC4R level" or "increase MC4R level" refer to increasing the level of MC4R in a cell contacted with a pharmacological chaperone specific for MC4R, relative to the level of MC4R in a cell (preferably of the same cell-type or the same cell, e.g., at an earlier time) not contacted with the pharmacological chaperone specific for MC4R.

The term "stabilize a proper conformation" refers to the ability of a MC4R pharmacological chaperone to induce or stabilize a conformation of a mutated MC4R protein that is functionally identical to the conformation of the wild-type MC4R protein. The term "functionally identical" means that while there may be minor variations in the conformation (almost all proteins exhibit some conformational flexibility in their physiological state), conformational flexibility does not result in (1) protein aggregation, (2) elimination through the endoplasmic reticulum-associated degradation pathway, (3) impairment of protein function, e.g., the ability to bind ligand and/or activate adenylyl cyclase activity and/or (4) improper transport within the cell, e.g., localization to the plasma membrane, to a greater or lesser degree than that of the wild-type protein.

The term "stable molecular conformation" refers to a conformation of a protein, i.e., MC4R, induced by a pharmacological chaperone, that provides at least partial wild-type function in the cell. For example, a stable molecular conformation of a mutant MC4R would be one where MC4R escapes from the ER and is trafficked to the cell membrane as for a wild-type MC4R, instead of misfolding and being degraded. In addition, a stable molecular conformation of a mutated MC4R may also possess full or partial MC4R activity, e.g., adenylyl cyclase activating activity for enhanced cAMP generation via its cognate physiologic G protein. However, it is not necessary that the stable molecular conformation have all of the functional attributes of the wild-type protein.

The term "MC4R activity" refers to the normal physiological function of a wild-type MC4R in a cell. For example, upon binding by an agonist, MC4R signals via interaction with a G-protein, $C\alpha_s$, and activation of adenylate cyclase (see e.g., VanLeeuwen, et al., *J. Biol. Chem.* 2003; 18: 15935-40). This results in the intracellular accumulation of cAMP and activation of protein kinase A (PKA). Such functionality can be tested by any method known in the art. For example, binding assays of the α-, β-, or γ-MSH ligand, or $^{125}$I-[Nle$^4$,D-Phe$^7$] α-MSH agonist to MC4R, or using adenylyl cyclase activation assays, or luciferase reporter gene assays, can be used to determine increases in intracellular cAMP. Cyclic AMP accumulation assays are well known in the art (see e.g., VanLeeuwen et al., *J. Biol. Chem.* 2003; 18: 15935-40).

"MC4R" refers to a polypeptide encoded by a nucleotide sequence having the sequence as depicted in any one of: SEQ ID NO: 1 (human; GenBank Accession No. BC069172); 3 (human; GenBank Accession No. NM_005912); 5 (rat; GenBank Accession No. NM_013099); or 7 (murine; GenBank Accession No. NM_016977).

An "MC4R polypeptide" also refers to an amino acid sequence as depicted in SEQ ID NOs: 2 (human; GenBank Accession No. AAI01803); 4 (human; GenBank Accession No. NM_005912); 6 (rat; GenBank Accession No. NM_013099); or 8 (murine; GenBank Accession No. AF201662), and any other amino acid sequence that encodes an MC4R polypeptide having the same function and ligand binding affinity as any one of SEQ ID NOs: 2, 4, 6 or 8.

The term "wild-type MC4R" refers to the nucleotide (SEQ ID NOs: 1, 3, 5 and 7) sequences encoding MC4R, and polypeptide (SEQ ID NOs: 2, 4, 6, and 8) sequences encoded by the aforementioned nucleotide sequences (human MC4R-GenBank Accession AAI01803; human MC4R-GenBank Accession No. NM_005912; rat MC4R-GenBank Accession No. NM_013099; and mouse MC4R-GenBank Accession AF201662), and any other nucleotide sequence that encodes MC4R polypeptide (having the same functional properties and binding affinities as the aforementioned polypeptide sequences), such as allelic variants in normal individuals, that have the ability to achieve a functional conformation in the ER, achieve proper localization within the cell, and exhibit wild-type activity (e.g., MC4R stimulation of cAMP accumulation).

As used herein the term "mutant MC4R" refers to a MC4R polypeptide translated from a gene containing a genetic mutation that results in an altered MC4R amino acid sequence. In one embodiment, the mutation results in a MC4R protein that does not achieve a native conformation under the conditions normally present in the ER, when compared with wild-type MC4R, or exhibits decreased stability or activity as compared with wild-type MC4R. This type of mutation is referred to herein as a "conformational mutation," and the protein bearing such a mutation is referred as a "conformational mutant." The failure to achieve this conformation results in MC4R protein being degraded or aggregated, rather than being transported through a normal pathway in the protein transport system to its native location in the cell or into the extracellular environment. In some embodiments, a mutation may occur in a non-coding part of the gene encoding MC4R that results in less efficient expression of the protein, e.g., a mutation that affects transcription efficiency, splicing efficiency, mRNA stability, and the like. By enhancing the level of expression of wild-type as well as conformational mutant variants of MC4R, administration of a MC4R pharmacological chaperone can ameliorate a deficit resulting from such inefficient protein expression.

Exemplary mutations (using the polypeptide of SEQ ID NO: 2 as a reference) include P78L, R165Q, and R165W. Other MC4R mutants include I125K, C271Y, T11A, A175T, I316L, I316S, I317T, N97D G98R, N62S, C271R, S58C, N62S, N97D, Y157S, I102S, L106P, L250Q, Y287X, P299H, S58C, CTCT at codon 211, and TGAT insertion at codon 244. In addition, other MC4R mutations (again using SEQ ID NO: 2 as a reference) include those described in Table 1, infra.

Certain tests may evaluate attributes of a protein that may or may not correspond to its actual in vivo activity, but nevertheless are appropriate surrogates of protein functionality, and weld-type behavior in such tests demonstrates evidence to support the protein folding rescue or enhancement techniques of the invention. One such activity in accordance with the invention is appropriate transport of a functional MC4R from the endoplasmic reticulum to the cell membrane.

The terms "endogenous expression" and "endogenously expressed" refers to the normal physiological expression of MC4R in cells in an individual not having or suspected of having a disease or disorder associated with MC4R deficiency, overexpression of a dominant negative mutant, or other defect, e.g., obesity, such as a mutation in MC4R nucleic acid or polypeptide sequence that alters, e.g., inhibits its expression, activity, or stability. This term also refers to the expression of MC4R in cells or cell types in which it is normally expressed in healthy individuals, and does not include expression of MC4R in cells or cell types, e.g., tumor cells, in which MC4R is not expressed in healthy individuals.

As used herein, the term "efficiency of transport" refers to the ability of a mutant protein to be transported out of the endoplasmic reticulum to its native location within the cell, cell membrane, or into the extracellular environment.

The terms "therapeutically effective dose" and "effective amount" refer to an amount sufficient to enhance protein processing in the ER (permitting a functional conformation), without inhibiting protein already expressed at the appropriate cellular location (in the case of an antagonist), or without inducing ligand-mediated receptor internalization of protein from the appropriate cellular location (in the case of an agonist), and enhance activity of the target protein, thus resulting n a therapeutic response in a subject. A therapeutic response may be any response that a user (e.g., a clinician) will recognize as an effective response to the therapy, including the foregoing symptoms and surrogate clinical markers. Thus, a therapeutic response will generally be an amelioration or inhibition of one or more symptoms of a disease or disorder, e.g., obesity or binge eating.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material, such as a MC4R nucleic acid or polypeptide, that has been isolated under conditions that reduce or eliminate unrelated materials, i.e., contaminants. For example, a purified protein is preferably substantially free of other proteins or nucleic acids with which it is associated in a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by conventional means, e.g., chromatography, gel electrophoresis, immunoassay, composition analysis, biological assay, and other methods known, in the art.

The term "Me" means methyl, "Et" means ethyl, and "Ac" means acetyl.

The term "halo", unless otherwise indicated, means fluoro, chloro, bromo or iodo, Preferred halo groups are fluoro, chloro and bromo.

The term "alkyl", unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "cycloalkyl", unless otherwise indicated, includes cyclic alkyl moieties wherein alkyl is as defined above. The use of the term "cycloalkyl" shall not be construed as limiting the term "alkyl" to non-cyclic moieties.

The term "alkenyl", unless otherwise indicated, includes alkyl moieties having at least one carbon-carbon double bond wherein alkyl is as defined above and including E and Z isomers of said alkenyl moiety.

The term "alkynyl", unless otherwise indicated, includes alkyl moieties having at least one carbon-carbon triple bond wherein alkyl is as defined above.

The term "alkoxy", unless otherwise indicated, includes O-alkyl groups wherein alkyl is as defined above.

The term "aryl", unless otherwise indicated, includes an organic radical derived from an aromatic hydrocarbon by removal of one hydrogen, such as phenyl or naphthyl.

The term "4 to 10 membered heterocyclic", unless otherwise indicated, includes aromatic and non-aromatic heterocyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition including 1-oxa-6-aza-spiro[2.5]oct-6-yl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The phrase "pharmaceutically acceptable salt(s)", unless otherwise indicated, includes salts of acidic or basic groups which may be present in a compound used in the methods of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, dislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts. Since a single compound may include more than one acidic or basic moiety, such a compound may include mono, di or tri-salts in a single compound.

Melanocortin 4 Receptor

Melanocortin (MC) receptors are members of the seven-transmembrane-domain G protein-coupled receptor superfamily that activate generation of the second messenger cyclic AMP (cAMP). There are five MC receptors isolated to date: MC1R, MC2R, MC3R, MC4R and MC5R. MC2R is the receptor for adrenocorticotropic hormone (ACTH). Human MC4R is 332 amino acids in length.

The melanocortin 4 receptor (MC4R) has been implicated in the regulation of body weight (Graham et al, Nat. Genetics 1997; 17: 273-4). MC4R is expressed in the brain, including the hypothalamus, which influences food intake. Signaling via MC4R stimulates anorexigenic neural pathways. MC4R null mice develop late onset obesity with hyperglycemia and hyperinsulinemia. Mice lacking one MC4R allele (heterozygotes) have intermediate body weight between wild-type and homozygous null mice. In humans, MC4R deficiency is the most common monogenic form of obesity (Farooqi et al., New Engl. J. Med. 2003; 348: 1085-95). Transgenic mice overexpressing an endogenous MC4R antagonist, agouti-related protein (AgRP), exhibited increased weight gain, food consumption, and body length compared with non-transgenic littermates (Ollman et al., Science 1997; 278: 135-37).

Numerous mutations, found mostly in obese individuals, have been identified in the human MC4R gene, including frameshift, nonsense and missense mutations (Nijenhuis et al., J. Biol. Chem. 2003; 278: 22939-45). At least two groups of researchers have confirmed that MC4R is mutated in about 5% of obese individuals. Carriers of MC4R mutations demonstrated hyperphagia and hyperinsulinemia, had above-average bone mineral density, and more rapid linear growth than control subjects matched for BMI. Farooqi et al. also have found that signaling properties of the mutant MC4R receptors correlated with the severity of obesity.

Several authors have now reviewed the recent advances in our understanding of the genetics of MC4R in early onset obesity (see e.g., Farooqi I S, O'Rahilly S, Int J Obes (Lond), 2005 October, 29(10), 1149-52; Govaerts C, Srinivasan S, Shapiro A, Zhang S, Picard F, Clement K, Lubrano-Berthelier C, Vaisse C, Peptides, 2005 October, 26(10), 1909-19; Tao Y X, Mol Cell Endocrinol, 2005 Jul. 15, 239(1-2), 1-14; Farooqi I S, O'Rahilly S, Annu Rev Med, 2005, 56, 443-58). For example, in one patient with severe early-onset obesity, an autosomal-dominant mode of inheritance of an MC4R mutation has been found to be due to a dominant-negative effect caused by receptor dimerization (Biebermann H, Krude H, Elsner A, Chubanov V, Gudermann T, Gruters A, Diabetes, 2003 December, 52(12), 2984-8).

Loss of function is expected for MC4R with some mutations, since most of the mutations identified to date are non-conservative amino acid substitutions. This has been demonstrated for several MC4Rs found in obese individuals. In addition, a number of mutations have been associated with reduced expression of MC4R at the cell surface (Gu et al., Diabetes 1999, 48: 635-399 Nijenhuis et al., supra). For example, in a screen of eleven MC4R missense mutations that were only found in obese individuals, and which were located outside of the N-terminal region of MC4R (which is not involved in ligand binding), ten exhibited lower specific binding at the cell surface to the labeled α-melanocyte stimulating hormone (α-MSH) ligand $^{251}$I-[Nle$^4$,D-Phe$^7$]α-MSH, compared with wild-type MC4R. Nijenhuis et al., supra, at 22941. The decreased specific binding was determined to reflect a lower cell surface expression, since the affinity for ligand among the mutants was largely similar to the wild-type receptor, as depicted in Table 1 below (IC$_{50}$ values in nM+/−S.E.):

TABLE 1

| | IC$_{50}$ | | | IC$_{50}$ | |
|---|---|---|---|---|---|
| Mutant | WT 55 ± 7.4 α-MSH | WT 9.1 ± 0.64 $^{125}$I-[Nle$^4$,D-Phe$^7$]α-MSH | Mutant | WT 55 ± 7.4 α-MSH | WT 9.1 ± 0.64 $^{125}$I-[Nle$^4$,D-Phe$^7$]α-MSH |
| T112M | 28 ± 2.7 | 5.4 ± 0.64 | I317T | 38 ± 3.0 | 7.8 ± 0.44 |
| V253I (A700G) | 43 ± 2.0 | 8.1 ± 0.25 | I301T | 24 ± 4.8 | 5.8 ± 0.78 |
| S30F/G252S | 67 ± 8.8 | 6.7 ± 0.30 | R165W (C886T) | 40 ± 13 | 8.7 ± 1.0 |
| L250Q | 5.8 ± 0.35 | 3.4 ± 0.69 | R165Q (C886A) | 40 ± 11 | 8.9 ± 1.2 |
| I170V | 59 ± 5.7 | 8.9 ± 1.7 | P78L | — | — |

Nijenhuis et al., J. Biol. Chem. 2003; 278: 22939-22945, at 22942.

Even two mutants with higher binding affinity (L250Q and T112M) demonstrated lower cell surface expression according to saturation binding experiments. In addition, all mutants demonstrated decreased maximal response (receptor activation as measured using an adenylyl cyclase assay) upon α-MSH binding. In particular, Nijenhuis et al. concluded from results of immunocytochemical data that the P78L, R165Q and R165W mutants are expressed, but are retained intracellularly.

An additional study identified the following MC4R mutations: I125K; C271Y; T11A (A434G); A175T; I316L; N97D; N62S; and C271R (Farooqi et al., *New Eng. J. Med.* 2003; 348; 1085-95). Of these mutations, all exhibited reduced activity, or no activity, in vitro evaluated using a luciferase reporter gene assay responsive to cAMP. However, this group found that three variants V103I; I251L; and T112M have no effect on MC4R signaling. Mutations associated with childhood, i.e., early onset obesity were S58C, N62S, Y157S, C271 Y, P78L, G98R that resulted in either decreased (S58C, N62S, Y157S, C271Y) or no (P78L, G98R) ligand binding, also demonstrated proportional impairments in [Nle$^4$,D-Phe$^7$]α-MSH-stimulated cAMP production (Tao et al., *Endocrinology* 2003; 144(10):4544-51).

A final study identified the following mutants in MC4R; 125 I251L (A1144C); F51L (T544C); M200V (A991G); T5T (C408T) (Branson et al., *New Eng. J. Med.* 2003; 348: 1096-1103).

In addition to obesity, MC4R has been implicated in binge eating. According to the Diagnostic and Statistical Manual of Mental Disorders-Text Revision (DSM-IV-TR™, Fourth Ed.), binge eating involves recurrent episodes of eating an abnormally large amount of food and experiencing feelings of lack of control over the behavior. In one study of 469 white obese subjects, it was found that while only a small percentage of obese subjects were diagnosed with binge-eating, all of the obese subjects with MC4R mutations were diagnosed with binge-eating (Branson, et al., supra).

MC4R Structure and Ligand Binding

Endogenous melanocortin agonists contain the sequence His-Phe-Arg-Trp, which is important for melanocortin receptor molecular recognition and stimulation. The molecular determinants of MC4R ligand binding were determined in one study by employing a large array of ligands (Nickolls et al., *Pharmacol Exp Ther* 2003; 304(3):1217-27). Molecular modeling of the receptor was used to identify Phe284, in transmembrane (TM) domain 7 (TM7), as a potential site of ligand interaction. Mutation of Phe284 to alanine reduced binding affinity and potency of peptides containing L-Phe by up to 71-fold but did not affect binding of linear peptides containing D-Phe. This data was consistent with a hydrophobic interaction between the Phe7 of α-MSH and Phe284. Second, the effect of a naturally occurring mutation in TM3 (I137T), which, as described above is linked to obesity, was examined. This mutation decreased affinity and potency or cyclic, rigid peptides but not more flexible peptides, consistent with an indirect effect of the mutation on the tertiary structure of the receptor. The residues that support ligand selectivity for the MC4R over the MC3R were also determined. Mutation of Ile125 (TM3) of the MC4R to the equivalent residue of the MC3R (phenylalanine) selectively decreased affinity and potency of MC4R-selective ligands. This effect was mirrored by the reciprocal MC3R mutation F157I. The magnitude of this effect indicates that this locus is not of major importance. However, it was proposed that an isoleucine/phenylalanine mutation may affect the orientation of Asp122, which has been identified as a major determinant of ligand binding affinity.

Others have determined that Tyr268 was required for the selective interaction with the endogenous MC4R antagonist Agouti protein, as well as, for the selectivity of another MC4R agonist (Oosterom et al., *J. Biol. Chem.* 2001; 276(2): 931-6). Agouti; protein is normally expressed in the skin and is a natural antagonist of the MC4R (Kiefer et al., *Biochemistry* 1997; 36: 9084-2090).

MC4R Agonists and Antagonists

According to the invention, MC4R agonists and antagonists include the compounds depicted in FIGS. 1-8 and 10 herein and further described in Examples 3 and 4 below.

Natural agonists (ligands) of MC4R include α-MSH, ACTH, β-MSH, and γ-MSH (in order from highest to lowest affinity). Other MC4R ligands, including agonists and antagonists, which have been described to date are predominantly peptides (U.S. Pat. No. 6,060,589) and cyclic peptide analogs (U.S. Pat. No. 6,613,874 to Mazur et al.). A series of MC4R peptide agonists have also been designed (Sun et al., *Bioorg Med Chem* 2004; 12(10):2671-7). In addition, Nijenhuis et al. (*Peptides* 2003; 24(2):271-80) described the development and evaluation of melanocortin antagonist compounds that were selective for the MC4R. One compound, designated Ac-Nle-Gly-Lys-D-Phe-Arg-Trp-Gly-NH(2) (SEQ ID NO:9), was found to be the most selective MC4R compound, with a 90- and 110-fold selectivity for the MC4R as compared to the MC3R and MC5R, respectively. Subsequent modification yielded compound Ac-Nle-Gly-Lys-D-Nal(2)-Arg-Trp-Gly-NH(2) (SEQ ID NO:10), a selective MC4R antagonist with 34-fold MC4R/MC3R and 109-fold MC4R/MC5R selectivity. Both compounds were active in vivo, and crossed the blood-brain barrier. Further, U.S. Pat. Nos. 6,054,556 and 5,731,408 describe families of agonists and antagonists for MC4R that are lactam heptapeptides having a cyclic structure.

Other high-affinity MC4R antagonists are described in Grieco et al. (*J Med Chem* 2002; 24:5287-94). These cyclic antagonists were designed based on the known high affinity antagonist SHU9119 (Ac-Nle4-[Asp5-His6-DNal(2')7-Arg8-Trp9-Lys10]-NH(2)) (SEQ ID NO: 11). The SHU9119 analogues were modified in position 6 (His) with non-conventional amino acids. One compound containing a Che substitution at position 6 is a high affinity MC4R antagonist ($IC_{50}$=0.48 nM) with 100-fold selectivity over MC3R. Another compound with a Cpe substitution at position 6 also was a high affinity MC4R antagonist ($IC_{50}$, =0.51 nM) with a 200-fold selectivity over MC3R. Molecular modeling was used to examine the conformational properties of the cyclic peptides modified in position 6 with conformationally restricted amino acids. See also, Grieco et al., *Peptides* 2006; 27(2):472-81.

Several non-peptide MC4R ligands have been disclosed in U.S. published patent applications 2003/0158209 to Dyck et al. and 2004/082590 to Briner et al. Also, U.S. Pat. No. 6,638,927 to Renhowe et al. describes small, low-molecular weight guanidobenzamides as specific MC4R agonists. Richardson et al. have described novel arylpiperizines that are agonists of MC4R (*J Med Chem* 2004; 47(3):744-55). U.S. Pat. No. 6,979,691 to Yu et al. and U.S. Pat. No. 6,699,873 to Maguire also describe non-peptide compounds which bind selectively to MC4R.

WO 99/55679 to Basu et al. discloses isoquinoline derivatives, small molecule non-peptide compounds, which show low (micromolar) affinities for the MC1R and MC4R, reduction of dermal inflammation induced by arachidonic acids, and reductions of body weight and food intake.

WO 99/64002 to Nargund et al. also discloses spiropiperidine derivatives as melanocortin receptor agonists, useful for the treatment of diseases and disorders such as obesity, diabetes, and sexual dysfunction.

Other non-peptide MC4R antagonists have been described. Thus, U.S. published patent applications 2003/0176425 and 2003/0162819 to Eisinger disclose novel 1,2,4-thiadiazole and 1,2,4-thiadiazolium derivatives, respectively, as MC4R antagonists or agonists. These applications also disclose use of these compounds to treat obesity.

Several antagonists of melanocortin receptors have been demonstrated to be competitive antagonists, i.e., competing for binding with a ligand. For example, the melanocortin antagonist agouti signaling protein (ASIP) was shown to have characteristics consistent with competitive antagonism observed at the hMC1R, and more complex behavior observed at the other receptors (Yang et al., *Mol. Endocrinology* 1997; 11(3): 274-280). Similarly, ACTH, the natural ligand for MC2R, cannot be out-competed for binding by $\alpha$-, $\beta$-, or $\gamma$-MSH (Abdel-Malek et al., *Cell. Mol. Life Sci.* 2001; 48: 434-41.

Other MC4R binding compounds are described in the following: Bednarek and Fong, *Exp Opn Ther Patents* 2004; 14: 327-36; Ujjainwalla et al., *Bioorg. Med. Chem. Lett.* 2005; 15(18):4023-8; WO 03/07949 (Merck); WO 03/61660 (Eli Lilly); WO 03/09847 (Amgen); WO 03/09850 (Amgen); WO 03/31410 (Neurocrine Biosciences); WO 03/94918 (Neurocrine Biosciences); WO 03/68738 (Neurocrine Biosciences); WO 03/92690 (Procter and Gamble); WO 03/93234 (Procter and Gamble); WO 03/72056 (Chiron); WO 03/66597 (Chiron); WO 03/66587 (Chiron); WO 03/66587 (Chiron); WO 02/67869 (Merck); WO 02/68387 (Merck); WO 02/00259 (Taisho); WO 02/92566 (Taisho); Tran et al, *Bioorg Med Chem Lett.* 2006 [epub ahead of print]; Pontillo et al., *Bioorg Med Chem Lett.* 2005; 15(23):5237-40; Pontillo et al., *Bioorg Med Chem Lett.* 2005; 15(10):2541-6; Pontillo et al., *Bioorg Med Chem Lett.* 2004; 14(22):5605-9; Cheung et al., *Bioorg Med Chem Lett.* 2005; 15(24):5504-8; Yan et al., *Bioorg Med Chem Lett.* 2004; 15(20): 4611-4; Hsiung et al., *Endocrinology.* 2005 December; 146(12):5257-66; and Todorovic et al., *Peptides.* 2005 October; 26(10):2026-36.

Specific MC4R non-peptide agonists or antagonists contemplated for use in the presently claimed methods are described in Sebhat et al., *J Med Chem* 2002; 45: 4589 (compounds 1 and 6); Richardson et al., *J Med Chem.* 2004; 47: 744 (compound 2); Arasasingham et al., *J Med Chem.* 2003; 46: 9 (compound 3); WO 02/062766 to Millennium Pharmaceuticals (compound 4); Pedemonte et al., *J. Clin. Inves.* 2005; 115: 2564-71 (compound 5); Tran et al., *Bioorg Med Chem Lett.* 2005; 15: 3434-38 (compound 7); Xi et al., *Bioorg Med Chem Lett.* 2004; 14: 377-81 (compound 8); Vos et al., *J. Med Chem.* 2004; 47: 1602-04 (compound 9); Pan et al., *Bioorg Med Chem Lett.* 2003; 11: 185 (compound 10); Marsilje et al., *Bioorg Med Chem Lett.* 2004. 14: 3721 (compound 11); Ujjainwalla et al., *Bioorg Med Chem Lett.* 2003; 133: 4431 (compound 12); Nickolls et al., *J Pharmacol Exp Therap.* 2005; 313: 1281-1288 (compounds 13-17); Schioth et al., *Biophys Biochem Res Comm.* 2003; 399-405 (compound 18); Benoit et al., *J. Neurosci.* 2000; 20: 3442-48 (compounds 19 and 20); Vos et al., *Bioorg Med Chem Lett.* 2006; 15: 2302 (compound 21); Tucci et al., *Bioorg Med Chem Lett* 2005; 15: 4389 (compound 22); Pontillo et al., *Bioorg Med Chem Lett.* 2005; 15: 4615-18 (compound 23); Chaki et al., *J Pharmacol Exp Ther.* 2003; 304: 818 (compound 24); (Chaki et al., *Pharmacol Biochem Behav.* 2005; 82: 621 (compound 25).

Compounds 1, 2, 5, 6, 8, 10, 12, 13-17, and 19 described above are MC4R agonists, while compounds 3, 4, 7, 9, 11, 18, and 20 are antagonists.

Specific MC4R peptide antagonists contemplated for use in the presently claimed methods are Ac-Cys-Glu-His-D-(2')Nal-Arg-Trp-Gly-Cys-Pro-Pro-Lys-Asp-NH(2) (SEQ ID NO: 12); Ac-Cys-Nle-Arg-His-D-(2')Nal-Arg-Trp-Gly-Cys-NH(2) (SEQ ID NO: 13); Ac-Cys-Glu-His-D-Phe (3,4-di-Cl)-Arg-Trp-Gly-Cys-Pro-Pro-Lys-Asp-NH(2) (SEQ ID NO: 14), Ac-Nle-c[Asp-Che-DNal(2')-Arg-Trp-Lys-NH(2) (SEQ ID NO: 15); Ac-Nle-c[Asp-Cpe-DNal(2')-Arg-Trp-Lys-NH(2) (SEQ ID NO: 16); cyclo(1-6)-suc-His-DPhe-Arg-Trp-Lys-NH(2) (SEQ ID NO: 17); and Ac-DArg[Cys-Glu-His-DPhe-Arg-Trp-Cys]-NH(2) (SEQ ID NO: 18).

Peptide-based agonists and antagonists with non-naturally occurring side chains and peptidomimetics are contemplated. See e.g., U.S. Pat. No. 5,650,489; see also, U.S. Pat. No. 6,090,912, especially at Section 5.5. For example, the side chains of compounds 18-20 and the side chains in the compound class depicted in FIG. 16 can be non-naturally occurring.

MC4R has been shown to undergo ligand-mediated receptor internalization (Gao et al., *J Pharmacol Exp Ther* 2003; 307(3):870-7). Preexposure of GT1-7 cells that express endogenous MC4R to the agonist $\alpha$-melanocyte-stimulating hormone ($\alpha$-MSH), resulted in impaired cAMP formation to a second challenge of $\alpha$-MSH (Shinyama et al., *Endocrinology* 2003; 144(4):1301-14). This was not seen with administration of an antagonist. Ligand-induced internalization is triggered in G-protein coupled receptors by phosphorylation of serine or threonine residues between the C-terminal segment and third intracellular loop. Phosphorylation promotes binding of beta-arrestins, which target receptors for internalization and degradation by lysosomes. Recent data demonstrate that the cytosolic tail of an attractin-like protein (ALP) binds the C-terminal domain of MC4R (Yeo et al., *Biochem. J.* 2003; 376). Thus, a chaperone which increases the stability of MC4R on the cell surface will be especially beneficial given the short half-life of the receptor on the surface.

It is further expected that chaperone that is an agonist that will reversibly bind to an MC4R polypeptide in the ER will not induce receptor internalization. Similarly, where the chaperone compound is an antagonist, it is expected that it will not inhibit receptor activity once the receptor is at the cell surface.

Methods of Treatment

The present invention also provides a method for treating a condition associated with reduced MC4R stability, such as obesity, or having risk factors for developing obesity, by administering to a subject in need of such treatment a chaperone to enhance stability and/or activity of MC4R. The individual to be treated can be an individual who does not exhibit a mutation in MC4R that affects folding and processing of MC4R, but who would benefit from increased MC4R stability on, e.g., neurons. The individual to be treated can also have a mutation in MC4R that affects folding and processing of the MC4R protein, and exhibits reduced MC4R stability on neurons.

Formulation, Dosage and Administration

A specific pharmacological chaperone for MC4R, i.e., an MC4R agonist or antagonist or other MC4R-binding compound as described above, or as identified through the screening methods of the invention as set forth below, is advantageously formulated in a pharmaceutical composition together with a pharmaceutically acceptable carrier. The chaperone may be designated as an active ingredient or therapeutic agent for the treatment of obesity or other disorder involving reduced MC4R cell surface expression or transport to the cell surface.

The concentration of the active ingredient (pharmacological chaperone) depends on the desired dosage and administration regimen, as discussed below. Exemplary dose ranges of the active ingredient are from about 0.01 mg/kg to about 250 mg/kg of body weight per day; from about 1 mg/kg to about 100 mg/kg per day; or from about 10 mg/kg to about 75 mg/kg per day.

Therapeutically effective compounds can be provided to a subject in standard formulations, and may include any pharmaceutically acceptable additives, such as excipients, lubricants, diluents, flavorants, colorants, buffers, and disintegrants. Standard formulations are well known in the art. See e.g., Remington's Pharmaceutical Sciences, 20th edition, Mack Publishing Company, 2000. The formulation may be produced in useful dosage units for administration by any route that will permit the therapeutic chaperone to cross the blood-brain barrier. Exemplary routes include oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration.

In one embodiment, an MC4R pharmacological chaperone, particularly those depicted in FIGS. 1-8 and 10 herein, is formulated in a solid oral dosage form. For oral administration, e.g., for a small molecule, the pharmaceutical composition may take the form of a tablet or capsule prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

In another embodiment, an MC4R chaperone is formulated for parenteral administration. The chaperone may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the formulations described previously, the chaperone may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In another embodiment, the chaperone can be delivered in a vesicle, particularly a liposome.

In another embodiment, the chaperone can be delivered in a controlled release manner. For example, a therapeutic agent can be administered using intravenous infusion with a continuous pump, in a polymer matrix such as poly-lactic/glutamic, acid (PLGA), in a pellet containing a mixture of cholesterol and the active ingredient (SilasticR™; Dow Corning, Midland, Mich.; see U.S. Pat. No. 5,554,601), by subcutaneous implantation, or by transdermal patch.

Combination Therapy. The pharmaceutical composition may also include other biologically active substances in combination with the candidate compound. Examples include but are not limited to sibutramine, orlistat (Xenical®), leptin, neuropeptide Y, cholecystokinin, or GLP-1.

Screening Assays for MC4R Pharmacological Chaperones

The present invention further provides a method for identifying a candidate chaperone compound that modulates the stability, activity, and/or cell surface localization of an MC4R polypeptide. In one embodiment, the present invention provides a method for identifying a chaperone for the MC4R protein, which comprises bringing a labeled or unlabeled test compound in contact with the MC4R protein or a fragment thereof and measuring the amount of the test compound bound to the MC4R protein or to the fragment thereof. This can be achieved for example as follows:

(a) contacting a first cell with a test compound for a time period sufficient to allow the cell to respond to said contact with the test compound;

(b) determining the conformational stability, activity, and/or cell surface localization of a MC4R polypeptide (or a fragment thereof comprising a ligand binding domain) in the cell (or on the cell surface) contacted in step (a); and (c) comparing the stability, activity, and/or cell surface localization of the MC4R polypeptide determined in step (b) to that of an MC4R polypeptide in a control cell that has not been contacted with the test compound;

wherein a detectable change in the stability, activity, and/or cell surface localization of the MC4R polypeptide in the first cell in response to contact with the test compound compared to the stability level of the MC4R polypeptide in the control cell that has not been contacted with the test compound, indicates that the test compound modulates the stability of the MC4R polypeptide and is a candidate compound for the treatment of a disorder associated with reduced MC4R stability or activity.

The cell can either be a host cell transformed with a non-endogenous wild-type or mutant MC4R, or an endogenously-MC4R-expressing cell, including mutant and wild-type MC4Rs. Such cells include the "obesity neurons" such as GT1-7 cells, described above, those described in MacKenzie et al., *Current Medicinal Chemistry—Immunology, Endocrine & Metabolic Agents* 2004; 4: 113-117, which endogenously express MC4R, or transformed cells expressing normal or mutated, tagged MC4R such as the HEK293 cells described in Blondet et al., *J Biochem* 2004; 135: 541-546 and below in the Examples.

In another embodiment, the present invention provides a method for identifying a chaperone for the MC4R protein, which comprises bringing a labeled test compound in contact with cells or a cell membrane fraction containing the MC4R protein, and measuring the amount of the labeled test compound bound to the cells or the cell membrane fraction.

Numerous high-throughput screening (HTS) methods can be employed to screen large numbers (e.g., hundreds, thousands, tens of thousands) of test compounds simultaneously for binding to a MC4R. A test compound can be, without limitation, a small organic or inorganic molecule (preferred), a peptide or a polypeptide (including an antibody, antibody fragment, or other immunospecific molecule), an oligonucleotide molecule (such as an aptamer), a polynucleotide molecule, or a chimera or derivative thereof. Test compounds which are candidate chaperones that specifically bind to an MC4R polypeptide can be identified using cell-based and/or cell-free assays. Several methods of automated assays that have been developed in recent years enable the screening of tens of thousands of compounds in a short period of time (see, e.g., U.S. Pat. Nos. 5,585,277, 5,679,582, and 6,020,141). For example, one group reported the identification of one arylpiperazine MC4R agonist through iterative directed screening of nonpeptidyl G-protein-coupled receptor biased libraries (Richardson et al., *J Med Chem* 2004; 47(3):744-55). Such HTS methods are particularly useful, e.g., in microarrays.

For screening, purified classes of compounds that may be identified include, but are not limited to, small molecules (i.e., organic or inorganic molecules which are less than about 2 kilodaltons (kD) in molecular weight, and, more preferably, less than about 1 kD in molecular weight). These are components of compound libraries.

As used herein, the term "lead compound" refers to a molecular entity selected from a primary screen of MC4R antagonists or agonists which may be effective on its own in stabilizing protein conformation of wild-type or mutant MC4R protein, or which may be modified by further development to generate an appropriate pharmaceutical compound.

Compound libraries. Libraries of high-purity small organic ligands and peptide agonists that have well-documented pharmacological activities are available from Sigma-Aldrich (LOPAC LIBRARY™ and LIGAND-SETS™). Also available from Sigma-Aldrich is an Aldrich Library of Rare Chemicals, which is a diverse library of more than 100,000 small-molecule compounds, including plant extracts and microbial culture extracts. Other compound libraries are available from Tripos (LeadQuest®) and TimTech (including targeted libraries for kinase modulators).

Other companies that supply or have supplied compound libraries of the type suitable for screening according to the invention include the following: 3-Dimensional Pharmaceuticals, Inc.; Advanced ChemTech; Abinitio PharmaSciences; Albany Molecular; Aramed Inc.; Annovis, Inc. (formerly Bearsden Bio, Inc.); ASINEX; AVANT Immunotherapeutics; AXYS Pharmaceuticals; Bachem; Bentley Pharmaceuticals; Bicoll Group; Biofor Inc.; BioProspect Australia Limited; Biosepra Inc.; Cadus Pharmaceutical Corp.; Cambridge Research Biochemicals; Cetek Corporation; Charybdis Technologies, Inc.; ChemBridge Corporation; ChemDiv, Inc.; ChemGenics Pharmaceuticals Inc.; ChemOvation Ltd.; ChemStar, Ltd.; Chrysalon; ComGenex, Inc.; Compugen Inc.; Cytokinetics; Dextra Laboratories Ltd.; Discovery Partners International Inc.; Discovery Technologies Ltd.; Diversa Corporation; Dovetail Technologies, Inc.; Drug Discovery Ltd.; ECM Pharma; Galilaeus Oy; Janssen Pharmaceutica; Jerini Bio Tools; J-Star Research; KOSAN Biosciences, Inc.; KP Pharmaceutical Technology, Inc.; Lexicon Genetics Inc.; Libris Discovery; MicroBotanica, Inc.; MicroChemistry Ltd.; MicroSource Discovery Systems, Inc.; Midwest Biotech Inc.; Molecular Design & Discovery; MorphoSys AG; Nanosyn, Inc.; Ontogen Corporation; Organix, Inc.; Pharmacopeia, Inc.; Pherin Pharmaceuticals; Phytera, Inc.; PTRL East, Inc.; REPLICor Inc.; RSP Amino Acid Analogues, Inc.; Sanofi-Synthelab (now Sanofi-Aventis) Pharmaceuticals; Sequitur, Inc.; Signature BioScience Inc.; Spectrum Info Ltd.; Talon Cheminformatics Inc.; Telik, Inc.; Tera Biotechnology Corporation; Tocris Cookson; Torrey Pines Institute for Molecular Studies; Trega Biosciences, Inc.; and WorldMolecules/MMD.

In addition, the Institute of Chemistry and Cell Biology (ICCB), maintained by Harvard Medical School, provides the following chemical libraries, including natural product libraries, for screening: Chem Bridge DiverSet E (16,320 compounds); Bionet 1 (4,800 compounds); CEREP (4,800 compounds); Maybridge 1 (8,800 compounds); Maybridge 2 (704 compounds); Peakdale 1 (2,816 compounds); Peakdale 2 (352 compounds); ChemDiv Combilab and International (28,864 compounds); Mixed Commercial Plate 1 (352 compounds); Mixed Commercial Plate 2 (320 compounds); Mixed Commercial Plate 3 (251 compounds); Mixed Commercial Plate 4 (331 compounds); ChemBridge Microformat (50,000 compounds); Commercial Diversity Set (5,056 compounds); NCI Collections: Structural Diversity Set, version 2 (1,900 compounds); Mechanistic Diversity Set (879 compounds); Open Collection 1 (90,000 compounds); Open Collection 2 (10,240 compounds); Known Bioactives Collections: NINDS Custom Collection (1,040 compounds); ICCB Bioactives 1 (489 compounds); SpecPlus Collection (960 compounds); ICCB Discretes Collections. The following ICCB compounds were collected individually from chemists at the ICCB, Harvard, and other collaborating institutions: ICCB1 (190 compounds); ICCB2 (352 compounds); ICCB3 (352 compounds); ICCB4 (352 compounds). Natural Product Extracts: NCI Marine Extracts (352 wells); Organic fractions—NCI Plant and Fungal Extracts (1,408 wells); Philippines Plant Extracts 1 (200 wells); ICCB-ICG Diversity Oriented Synthesis (DOS) Collections; DDS1 (DOS Diversity Set) (9600 wells).

There are numerous techniques available for creating more focused compound libraries rather than large, diverse ones. Chemical Computing Group, Inc. (Montreal) has developed software with a new approach to high-throughput drug design. The company's method uses high-throughput screening (HTS) experimental data to create a probabilistic QSAR (Quantitative Structure Activity Relationship) model, which is subsequently used to select building blocks in a virtual combinatorial library. It is based on statistical estimation instead of the standard regression analysis.

In addition, ArQule, Inc. (Woburn, Mass.) also has integrated technologies to perform high-throughput, automated production of chemical compounds and to deliver these compounds of known structure and high purity in sufficient quantities for lead optimization. Its AMAP™ (Automated Molecular Assembly Plant) performs high-throughput chemical syntheses for each phase of compound discovery.

Similarly compounds are often provided on online databases or on CD-ROM's for selective "cherry picking" of compounds. See, e.g., Abinitio PharmaSciences; ActiMol; Aral Biosynthetics; ASDI Biosciences; Biotechnology Corporation of America; Chembridge; ChemDiv; Florida Center—Heterocyclic Compounds; Microsource/MSDI, NorthStar; Peakdale; Texas Retaining Group; Zelinsky Institute; Advanced ChemTech; Ambinter; AnalytiCon Discovery; Aurora Fine Chemicals; Biofocus; Bionet/Key; Comgenex; Key Organics; LaboTest; Polyphor; SPECS and Biospecs; and Bharavi Laboratories.

Microarrays

In one embodiment, HTS screening for MC4R chaperones employs microarrays.

Protein arrays.

Protein arrays are solid-phase, binding assay systems using immobilized proteins on various surfaces that are selected for example from glass, membranes, microtiter wells, mass spectrometer plates, and beads or other particles. The binding assays using these arrays are highly parallel and often miniaturized. Their advantages are that they are rapid, can be automated, are capable of high sensitivity, are economical in their use of reagents, and provide an abundance of data from a single experiment.

Automated multi-well formats are the best-developed HTS systems. Automated 96- or 384-well plate-based screening systems are the most widely used. The current trend in plate-based screening systems is to reduce the volume of the reaction wells even further, and increase the density of the wells per plate (96 wells to 384 wells to 1,536 wells per plate). The trend results in increased throughput, dramatically decreased bioreagent costs per compound screened, and a decrease in the number of plates that need to be managed by automation. For a description of protein arrays that can be used for HTS, see e.g.: U.S. Pat. Nos. 6,475,809; 6,406,921; and 6,197,599; and International Publication Nos. WO 00/04389 and WO 00/07024.

For construction of arrays, sources of MC4Rs or fragments thereof, whether in wild-type or mutant form, can include cell-based expression systems for recombinant proteins, purification from natural sources, production in vitro by cell-free translation systems, and synthetic methods for making MC4R peptides. For capture arrays and protein function analysis, it is often the case that MC4R polypeptides are correctly folded and functional. This is not always the case, e.g., where recombinant proteins are extracted from bacteria under denaturing conditions; other methods (isolation of natural proteins, cell free synthesis) generally retain functionality. However, arrays of denatured proteins can still be useful in screening chaperones since the chaperone will likely bind to the mutated protein while it is not folded into its proper conformation.

The immobilization method used is preferably applicable to MC4R polypeptides of different properties (e.g., wild-type, mutant, full-length, partial-length fragments, hydrophilic, hydrophobic, etc.), amenable to high throughput and automation, and generally compatible with retention of chaperone-binding ability. Both covalent or non-covalent methods of MC4R protein immobilization can be used. Substrates for covalent attachment include, e.g., glass slides coated with amino- or aldehyde-containing silane reagents (Telechem). In the Versalinx™ system (Prolinx), reversible covalent coupling is achieved by interaction between the protein derivatized with phenyldiboronic acid, and salicylhydroxamic acid immobilized on the support surface. Covalent coupling methods providing a stable linkage can be applied to a range of proteins. Non-covalent binding of unmodified protein occurs within porous structures such as HydroGel™ (PerkinElmer), based on a 3-dimensional polyacrylamide gel.

Cell-Based Arrays.

Cell-based arrays combine the technique of cell culture in conjunction with the use of fluidic devices for measurement of cell response to test compounds in a sample of interest, screening of samples for identifying molecules that induce a desired effect in cultured cells, and selection and identification of cell populations with novel and desired characteristics. High-throughput screening (HTS) can be performed on fixed cells using fluorescent-labeled antibodies, biological ligands or candidate chaperones and/or nucleic acid hybridization probes, or on live cells using multicolor fluorescent indicators and biosensors. The choice of fixed or live cell screens depends on the specific cell-based assay required.

There are numerous single- and multi-cell-based array techniques known in the art. Recently-developed techniques such as micro-patterned arrays (described, e.g., in International PCT Publications WO 97/45730 and WO 98/38490) and microfluidic arrays provide valuable tools for comparative cell-based analysis. Transfected cell microarrays are a complementary technique in which array features comprise clusters of cells overexpressing defined cDNAs. Complementary DNAs cloned in expression vectors are printed on microscope slides, which become living arrays after the addition of a lipid transfection reagent and adherent mammalian cells (Bailey et al., *Drug Discov. Today* 2002; 7(18 Suppl): S113-8). Cell-based arrays are described in detail in, e.g., Beske, *Drug Discov. Today* 2002; 7(18 Suppl): S131-5; Sundberg et al., *Curr. Opin. Biotechnol.* 2000; 11: 47-53; Johnston et al., *Drug Discov. Today* 2002; 7: 353-63'; U.S. Pat. Nos. 6,406,840 and 6,103,479, and U.S. published patent application no. 2002/0197656. For cell-based assays specifically used to screen for modulators of ligand-gated ion channels, see Mattheakis et al., *Curr. Opin. Drug Discov. Devel.* 2001; 1: 124-34; and Baxter et al., *J. Biomol. Screen.* 2002; 7: 79-85.

Detectable Labels.

For detection of molecules such as candidate MC4R chaperones using screening assays, a functional assay can be used to follow unlabeled molecules as described elsewhere herein. A molecule-of-interest (e.g., a small molecule, an antibody, or a polynucleotide probe) or a library of same can also be detectably labeled with an atom (e.g., a radionuclide), a detectable molecule (e.g., fluorescein), or a complex that, due to a physical or chemical property, serves to indicate the presence of the molecule of interest. A molecule can also be detectably labeled when it is covalently bound to a "reporter" molecule (e.g., a biomolecule such as an enzyme) that acts on a substrate to produce a detectable product. Detectable labels suitable for use in the present invention include any composition detectable by spectroscopic, photochemical, biochemical, immunochemical, electrical, optical or chemical means. Labels useful in the present invention include, but are not limited to, biotin for staining with labeled avidin or streptavidin conjugate, magnetic beads (e.g., Dynabeads™), fluorescent dyes (e.g., fluorescein, fluorescein-isothiocyanate (FITC), Texas red, rhodamine, green fluorescent protein, enhanced green fluorescent protein, lissamine, phycoerythrin, Cy2, Cy3, Cy3.5, Cy5, Cy5.5, Cy7, Fluor X from Amersham, SyBR Green I & II from Molecular Probes, and the like), radiolabels (e.g., $^3$H, $^{125}$I, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horse radish peroxidase, and the like), substrates, cofactors, inhibitors, chemiluminescent groups, chromogenic agents, and colorimetric labels such as colloidal gold or colored glass or plastic (e.g., polystyrene, polypropylene, latex, etc.) beads. Examples of patents describing the use of such labels include U.S. Pat. Nos. 3,817, 837; 3,850,752; 3,939,350; 3,996,345; 4,277,437; 4,275,149; and 4,366,241.

Means of detecting such labels are known to those of skill in the art. For example, radiolabels and chemiluminescent labels can be detected using photographic film or scintillation counters; fluorescent markers can be detected using a photodetector to detect emitted light (e.g., as in fluorescence-activated cell sorting, FACS); and enzymatic labels can be detected by providing the enzyme with a substrate and detecting, e.g., a colored reaction product produced by the action of the enzyme on the substrate.

Stability, Localization and Activity Assays

As indicated previously, enhanced stability of MC4R can be determined by measuring an increase in cellular MC4R polypeptide, by determining an increase in trafficking to the cell surface, e.g., as determined by increased cell surface expression, or by determining increased MC4R activity. Non-limiting exemplary methods for assessing each of the foregoing are described below.

Determining MC4R Intracellular Stability.

Methods for determining intracellular MC4R protein levels are well-knows in the art. Such methods include Western blotting, immunoprecipitation followed by Western blotting (IP Western), or immunofluorescence using a tagged MC4R protein.

Determining MC4R Trafficking.

Assessing trafficking of proteins through the biosynthetic pathway can be achieved e.g., using pulse-chase experiments with $^{35}$S-labeled receptor protein, in conjunction with glycosidases; or by indirect or direct immunofluorescence to determine protein modification during trafficking. These and other methods are described for example in *Current Protocols in Cell Biology* 2001; John Wiley & Sons.

Methods for detecting impaired trafficking of proteins are well known in the art. For example, for proteins which are N- and/or O-glycosylated in the Golgi apparatus, pulse-chase metabolic labeling using radioactively labeled proteins, combined with glycosidase treatment and immunoprecipitation, can be used to detect whether the proteins are undergoing full glycosylation in the Golgi, or whether they are being retained in the ER instead of trafficking to the Golgi for further glycosylation.

Sensitive methods for visually detecting cellular localization also include fluorescent microscopy using fluorescent proteins or fluorescent antibodies. For example, MC4R proteins of interest can be tagged with e.g., green fluorescent protein (GFP), cyan fluorescent protein, yellow fluorescent protein, and red fluorescent protein, followed by multicolor and time-lapse microscopy and electron microscopy to study the fate of these proteins in fixed cells and in living cells. For a review of the use of fluorescent imaging in protein trafficking, see Watson et al., *Adv Drug Deliv Rev* 2005; 57(1):43-61. For a description of the use of confocal microscopy for intracellular co-localization of proteins, see Miyashita et al., *Methods Mol Biol.* 2004; 261:399-410.

Fluorescence correlation spectroscopy (FCS) is an ultra-sensitive and non-invasive detection method capable of single-molecule and real-time resolution (Vukojevic et al., *Cell Mol Life Sci* 2005; 62(5): 535-50). SPFI (single-particle fluorescence imaging) uses the high sensitivity of fluorescence to visualize individual molecules that have been selectively labeled with small fluorescent particles (Cherry et al., *Biochem Soc Trans* 2003; 31(Pt 5): 1028-31). For localization of proteins within lipid rafts, see Latif et al., *Endocrinology* 2003; 144(11): 4725-8. For a review of live cell imaging, see Hariguchi, *Cell Struct Funct* 2002; 27(5):333-4.

Fluorescence resonance energy transfer (FRET) microscopy is also used to study the structure and localization of proteins under physiological conditions (Periasamy, *J Biomed Opt* 2001; 6(3): 287-91).

For plasma membrane resident proteins, less sensitive assays can be used to detect whether they are present on the membrane. Such methods include immunohisto-chemistry of fixed cells, or whole-cell labeling using radiolabeled ligand (e.g., $^{125}$I).

Determining MC4R Cell Surface Expression.

Once a candidate compound has been identified, the next step is determining whether the candidate compound can enhance the amount of MC4R trafficked to the cell surface. Numerous assays can be used to evaluate cell surface receptor expression quantitatively. For example, radioactive ligand binding assays, using e.g., $^{125}$I-MSH, can be used to determine binding to either whole cells expressing MC4R or to cell membrane fractions. See U.S. published application 2003/0176425 for a description of one exemplary method; see also Chhajlani, *Peptides.* 1996; 17(2):349-51. In addition, immunofluorescence staining, using either labeled antibodies or labeled MC4R (e.g., FLAG-tagged MC4R), may also be used. Another well-known method is fluorescence-activated cell sorting (FACS), which sorts or distinguishes populations of cells using labeled antibodies against cell surface markers. See also, Nijenhuis et al., supra.

Determining an Increase in MC4R Activity.

MC4R activity can be determined using, e.g., cAMP activation/accumulation assays (see e.g., VanLeeuwen et al., *J Biol Chem* 2003; 278(18): 15935-40) or by measuring an increase in transcription of one or more genes activated by cAMP, or by measuring reporter gene expression by operatively linking a reporter gene such as luciferase to a cAMP response element (CRE) (see e.g., Lee et al., *Eur J Biochem* 2001; 268(3):582-91). In addition, it is also known that MC4R stimulates TNF-α secretion in melanophores. Therefore, MC4R activity in response to a candidate compound can be evaluated by measuring TNF-α secretion (see e.g., Ignar et al., *Peptides* 2003 May; 24(5):709-16).

Lastly, melanophores provide a rapid and sensitive bioassay for melanocortin agonists and antagonists. This method is based on the measurement of pigment granule dispersion induced by α-MSH, as determined by changes in optical density (Quillan et al., *PNAS U.S.A.* 1995; 92: 2894; and Potenza et al., *Pigment Cell Res* 1992; 5: 372).

Molecular Biology Definitions

In accordance with the present invention there may be employed conventional molecular biology, microbiology, and recombinant DNA techniques within the skill of the art. These techniques are generally useful for the production of recombinant cells expressing wild-type or mutant MC4R's for use in screening assays. Such techniques are explained fully in the literature. See, e.g., *Sambrook Fritsch & Maniatis, Molecular Cloning: A Laboratory Manual*, Second Edition (1989) Cold Spring Harbor Laboratory Press, Cold Spring Harbor, N.Y. (herein "Sambrook et al., 1989"); *DNA Cloning, A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); Transcription And Translation (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994); and later editions of each, where available.

The term "host cell" means any cell of any organism that is selected, modified, transformed, grown, used, or manipulated in any way, for the production of a desired substance by the cell, for example the expression by the cell of a gene, a DNA or RNA sequence, a protein, or an enzyme. According to the present invention, the host cell is modified to express a mutant or wild-type MC4R nucleic acid and polypeptide. Host cells can further be used for screening or other assays. Exemplary host cells for use in the present invention are HEK293 cells, COS cells, and CHO cells.

A "recombinant DNA molecule" is a DNA molecule that has undergone a molecular biological manipulation.

The MC4R polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the all. Non-limiting examples of such modifications include: methylation, "caps," substitution of one or more of the naturally occurring nucleotides with an analog, and internucleotide modifications such as, for example, those with uncharged linkages (e.g., methyl phosphonates, phosphotriesters, phosphoroamidates, carbonates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like. The nucleic acids may also be altered at one or more bases by e.g., site-directed mutagenesis to facilitate molecular biology associated with use of the molecules.

A "coding sequence" or a sequence "encoding" an expression product, such as an MC4R RNA or polypeptide, is a nucleotide sequence that, when expressed, results in the production of that RNA or polypeptide, e.g., the MC4R nucleotide sequence encodes an amino acid sequence for an MC4R polypeptide (protein). A coding sequence for the protein may include a start codon (usually ATG) and a stop codon.

The term "gene," also called a "structural gene" means a DNA sequence that codes for or corresponds to a particular sequence of amino acids which comprise all or part of one or more MC4R proteins, and may or may not include regulatory DNA sequences, such as promoter sequences, which determine for example the conditions under which the MC4R gene is expressed.

The terms "express" and "expression," when used in the context of producing an amino acid sequence from a nucleic acid sequence, means allowing or causing the information in a MC4R gene or DNA sequence to become manifest, for example producing an MC4R protein by activating the cellular functions involved in transcription and translation of the corresponding MC4R gene or DNA sequence. A DNA sequence is expressed in or by a cell to form an "expression product" such as an MC4R protein. The expression product itself, e.g., the resulting protein, may also be said to be "expressed" by the cell. An expression product can be characterized as intracellular, extracellular or secreted. According to the present invention, MC4R is expressed at the cell surface of neurons.

The term "intracellular" means something that is inside a cell. The term "extracellular" means something that is outside a cell. A substance is "secreted" by a cell if it appears in significant measure outside the cell, from somewhere on or inside the cell.

The term "heterologous" refers to a combination of elements not naturally occurring in combination. For example, heterologous DNA refers to DNA not naturally located in the cell, or in a chromosomal site of the cell. Preferably, the heterologous DNA includes a gene foreign to the cell. A heterologous expression regulatory element is an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed, e.g., an *E. coli* cell.

The term "transformation" refers to the process by which DNA, i.e., a nucleic acid encoding an MC4R polypeptide, is introduced from the surrounding medium into a host cell.

The term "transduction" refers to the introduction of DNA, i.e., a nucleic acid encoding an MC4R polypeptide, into a prokaryotic host cell, e.g., into a prokaryotic host cell via a bacterial virus, or bacteriophage. A prokaryotic or eukaryotic host cell that receives and expresses introduced DNA or RNA has been "transformed" or "transduced" and is a "transformant" or a "clone." The DNA or RNA introduced into a host cell can come from any source, including cells of the same genus or species as the host cell, or cells of a different genus or species, or synthetic sequences.

The term "recombinantly engineered cell" refers to any prokaryotic or eukaryotic cell that has been manipulated to express or overexpress the nucleic acid of interest, i.e., a nucleic acid encoding an MC4R polypeptide, by any appropriate method, including transfection, transformation or transduction. This term also includes endogenous activation of a nucleic acid in a cell that does not normally express that gene product or that expresses the gene product at a suboptimal level.

The term "transfection" means the introduction of a foreign (i.e., extrinsic or extracellular, nucleic acid into a cell. The "foreign" nucleic acid includes a gene, DNA or RNA sequence to a host cell, so that the host cell will replicate the DNA and express the introduced gene or sequence to produce a desired substance, typically a protein or enzyme coded by the introduced gene or sequence. The introduced gene, i.e., a nucleic acid encoding, an MC4R polypeptide, or sequence may also be called a "cloned" gene or sequence, may include regulatory or control sequences, such as start, stop, promoter, signal, secretion, or other sequences used by a cell's genetic machinery. The gene or sequence may include nonfunctional sequences or sequences with no Known function. DNA may be introduced either as an extrachromosomal element or by chromosomal integration or a host cell that receives and expresses introduced DNA or RNA.

Depending on the host cell used, transformation or transfection is done using standard techniques appropriate to such cells. The calcium treatment employing calcium chloride, as described in section 1.82 of Sambrook et al., 1989 supra, is generally used for bacterial cells that contain substantial cell-wall barriers. Another method for transformation employs polyethylene glycol/DMSO, as described in Chung and Miller (*Nucleic Acids Res.* 1988, 16:3580). Yet another method is the use of the technique termed electroporation. Alternatively, where a viral vector is used, the host cells can be infected by the virus containing the gene of interest.

The terms "vector," "cloning vector" and "expression vector" mean the vehicle by which a DNA or RNA sequence (e.g., an MC4 gene) can be introduced into a host cell, so as to transform the host and promote expression (e.g., transcription and translation) of the introduced sequence. Vectors include plasmids, phages, viruses, etc.; they are well known in the art.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase.

A coding sequence is "under the control of" or "operatively associated with" transcriptional and translational control sequences in a cell when RNA polymerase transcribes the coding sequence into mRNA, which is then trans-RNA spliced (if it contains introns) and translated into the protein encoded by the coding sequence.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform bacterial strains, and successful transformants are selected by ampicillin or tetracycline resistance where appropriate. Plasmids from the transformants are prepared, analyzed by restriction endonuclease digestion, and/or sequenced by the method of Sanger et al. (Proc. Natl. Acad. Sci. USA 1977, 74:5463-5467) or Messing et al. (Nucleic Acids Res. 1981, 9:309), or by the method of Maxam et al. (Methods in Enzymology 1980, 65:499). Host cells are transformed with the above-described expression vectors of this invention and cultured in conventional nutrient media modified as appropriate for the promoter utilized.

EXAMPLES

The present invention is further described by means of the examples, presented below. The use of such examples is illustrative only and in no way limits the scope and meaning of the invention or of any exemplified term. Likewise, the invention is not limited to any particular preferred embodiment described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

Generation of Cell Lines Expressing MC4R Folding Mutants

In order to determine whether some MC4R mutants result in conformational defects of MC4R, MC4R nucleic acids containing the various mutants are transfected into HEK-293T and COS-7 cells and their cell surface expression and activity evaluated. Those cell lines in which reduced or absent cell surface expression is observed are evaluated further to determine the intracellular presence and/or location of the MC4R polypeptide.

Methods

Generation of MC4R Mutants.

A cDNA encoding a wild-type MC4R (e.g., SEQ ID NO: 1) is modified using known techniques in the art (e.g., PCR, site-directed mutagenesis) to generate mutant MC4R cDNAs containing alterations in the nucleotides which result in, e.g., one of the following MC4R mutant polypeptides: P78L, R165Q, R165W, I125K, C271Y, T11A, A175T, I316L, I316S, I317T, N97D, G98R, N62S, C271R, S58C, N62S, N97D, Y157S, I102S, L106P, L250Q, Y287X, P299H, S58C, CTCT at codon 211, and/or TGAT insertion at codon 244. Such mutants can also be fused to a fluorescent tag, such as GFP, as described in Blondet et al. *J Biochem* (Tokyo) 2004; 135(4):541-6, or FLAG-tagged, as described by VanLeeuwen et al., *J. Biol. Chem.* 2003; 278: 15935-15940, or tagged-with an enzyme such as luciferase.

Cell Culture and Transfection.

Such mutant MC4R nucleic acids are cloned into an appropriate expression vector, e.g., pCDNA3.1 (Invitrogen, Carlsbad, Calif.), according to the manufacturer's instructions. Transfection of cells is accomplished using LipofectAMINE (Invitrogen), and permanently transfected clonal cell lines are selected by resistance to the neomycin analog G418.

Briefly, HEK-293T and COS-7 cells are maintained in Dulbecco's modified Eagle's medium (with glutamine; Invitrogen) supplemented with 10% fetal bovine serum, 100 units/ml penicillin, and 100 µg/ml streptomycin (Invitrogen). Cells are incubated at 37° C. in humidified air containing 5% CO2. Cells are generally at 70-80% confluence on the day of transfection.

GFP Tagged MC4R.

Green fluorescent protein (GFP) cDNA is available from BD Biosciences (San Jose, Calif.) or Clontech (Palo Alto, Calif.). GFP is fused in frame to the C terminus of human MC4R with the C-terminal termination codon removed, according to the manufacturer's instructions. The chimeric MC4R-GFP fusion protein construct is then transfected as above. A luciferase construct is similarly employed.

Detection of Localization of MC4R Mutants.

Binding experiments to determine cell surface localization are performed using conditions described previously (Yang et al., *J Biol Chem* 1997; 272: 23000-23010). Briefly, $2 \times 10^5$ cpm of $^{125}$I-NDP-MSH (Amersham Biosciences, Piscataway, N.J.) is used in combination with non-radiolabeled ligands NDP-MSH, AgRP 87-132, or AgRP 110-117. Binding reactions are terminated by removing the media and washing the cells twice with minimal essential medium containing 0.2% bovine serum albumin. The cells are then lysed with 0.2 N NaOH, and the radioactivity in the lysate is quantified in an analytical-counter. Nonspecific binding is determined by measuring the amount of 125I label bound in the presence of $10^{-6}$ M unlabeled ligand. Additional, FACS can be used as described below in Example 4. Specific binding is calculated by subtracting nonspecifically bound radioactivity from total bound radioactivity. The maximum binding (Bmax) can be calculated using the equation Bmax=[NDP-MSH specific binding]/([NDP-MSH]/(Kd+[NDP-MSH]). Ki=IC50/1+ligand concentration/Kd.

Where the MC4R mutant is fluorescently tagged, confocal microscopy is used to monitor intracellular trafficking of tagged MC4R (Blondet et al., *J Biochem* 2004; 135: 541-546; or Gao et al., *J Pharmacol Exp Ther* 2003; 307(3):870-7).

Briefly, cells are grown in chamber coverglasses 24 to 48 h before the experiments. After appropriate treatments, cells are washed with cold PBS and fixed in formalin for 20 minutes, and observed on an LSM 510 META laser scanning microscope (Carl Zeiss, Thornwood, N.Y.). Fluorescence of GFP is excited using a 488-nm argon/krypton laser, detected with a band pass filter of 500 to 550 nm. Red signal is excited with a HeNe laser at 543 nm and fluorescence is detected with a 565 to 615 band pass filter.

The digitally-acquired images are quantitated using a Scion Image Beta 4.02. The original green fluorescence confocal images are converted to grayscale and median filtering is performed. Each pixel is assigned an intensity value ranging from 0 (black) to 255 (white). The cell surface and total cellular fluorescence intensity are measured after manually selecting the corresponding area. The subcellular distribution of MC4R-GFP is expressed as a ratio of cell surface fluorescence intensity to total cellular fluorescence intensity. A decrease in the ratio indicates receptor internalization.

Using these methods, folding mutants of MC4R are identified that would be candidates for chaperone-mediated rescue.

Example 2

Structures of Agonists and Antagonists of MC4R

Figure 1:
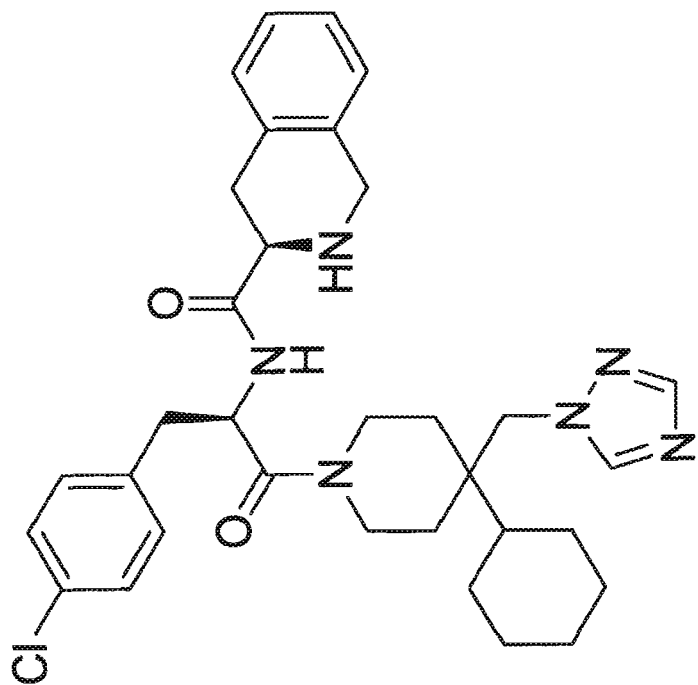
FIG. 1. An agonist of the rat and human melanocortin-4 receptors, as reported by Sebhat, 2002, *J. Med Chem*, 45, 4589-4593 (compound 1).

Potential agonists and antagonists of MC4R were selected based on the review of published patent and literature references (in particular, Bednarek and Fong, *Exp. Opn. Therapeutic Patents* 2004; 14(3): 327-326 and WO 02/062766). Criteria used in selecting the compounds described herein included published $IC_{50}$ data, in vivo animal data, and bioavailability data (e.g., pharmacokinetics), where available.

a) Synthesis of the Agonist of FIG. 1 (Compound 1)

Selection of this compound, known as THIQ, was based on the following data:

| Name | MC4R Activity | | | PK | Reference(s) |
|---|---|---|---|---|---|
| | $IC_{50}$ (nM) | $EC_{50}$ (nM) | $E_{max}$ (%) | | |
| THIQ/ compound 1 | 1.2 | 2.5 | 97 | % F 14<br>$V_d$ 3.6 L/kg<br>Cl 84 mLmin/kg<br>$t_{1/2}$ 0.6 h | Van der Ploeg et al (2002) PNAS 99: 11381.<br>Sebhat et al (2002) J Med Chem 45: 4589. |

Figure 2:
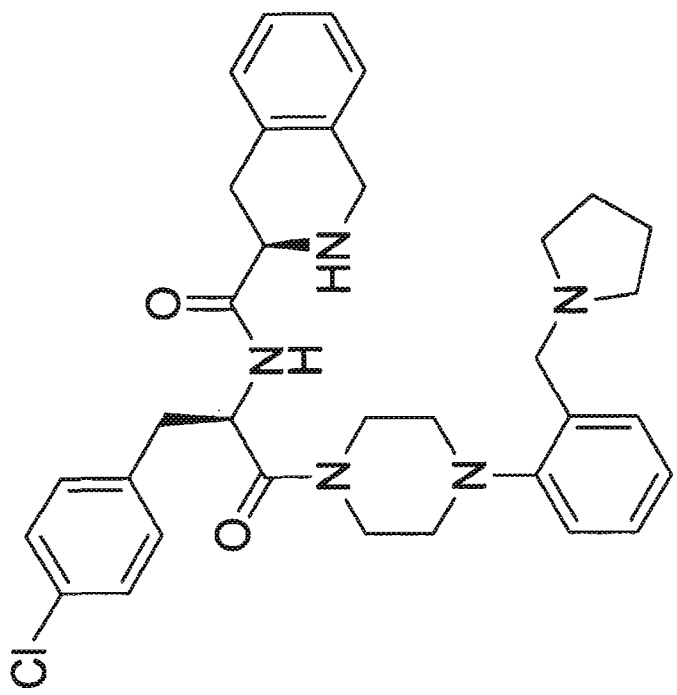
FIG. 2. An agonist of human MC4R, as reported by Richardson, 2004, *J Med Chem* 47, 744-755 (compound 2).
Figure 3:
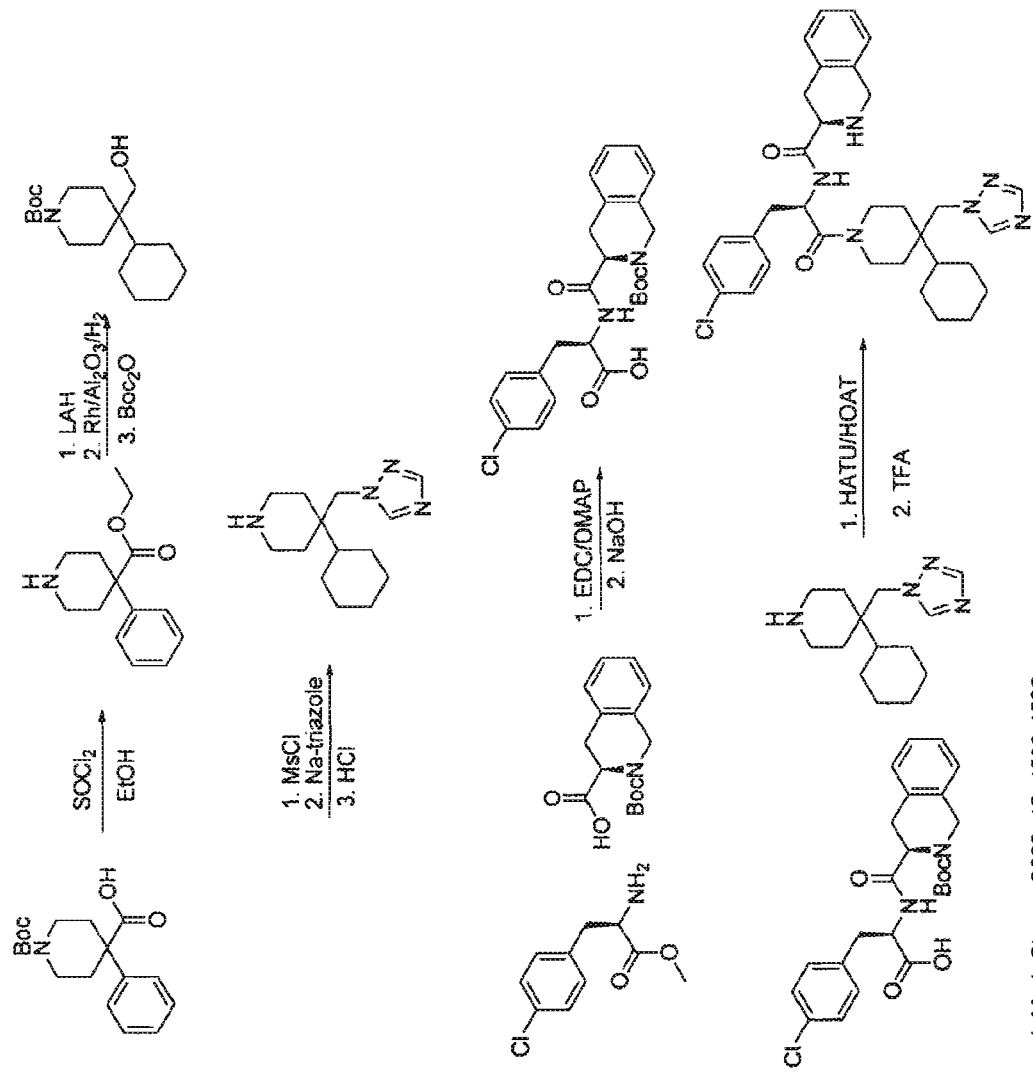
FIG. 3. Synthetic scheme for compound 1.

Synthesis of this molecule (11-steps) was performed based on the scheme depicted in FIG. 3.

b) Synthesis of the Agonist of FIG. 2 (Compound 2)

Selection of this known compound, referred to as compound 2, was based on the following data:

| Name | MC4R Activity | | | PK | Reference(s) |
|---|---|---|---|---|---|
| | $K_i$ (Nm) | $EC_{50}$ (nM) | $E_{max}$ (%) | | |
| Compound 2 | 24 | 39 | ND | ND | Richardson et al (2004) J Med Chem 47: 744. |

Figure 4:
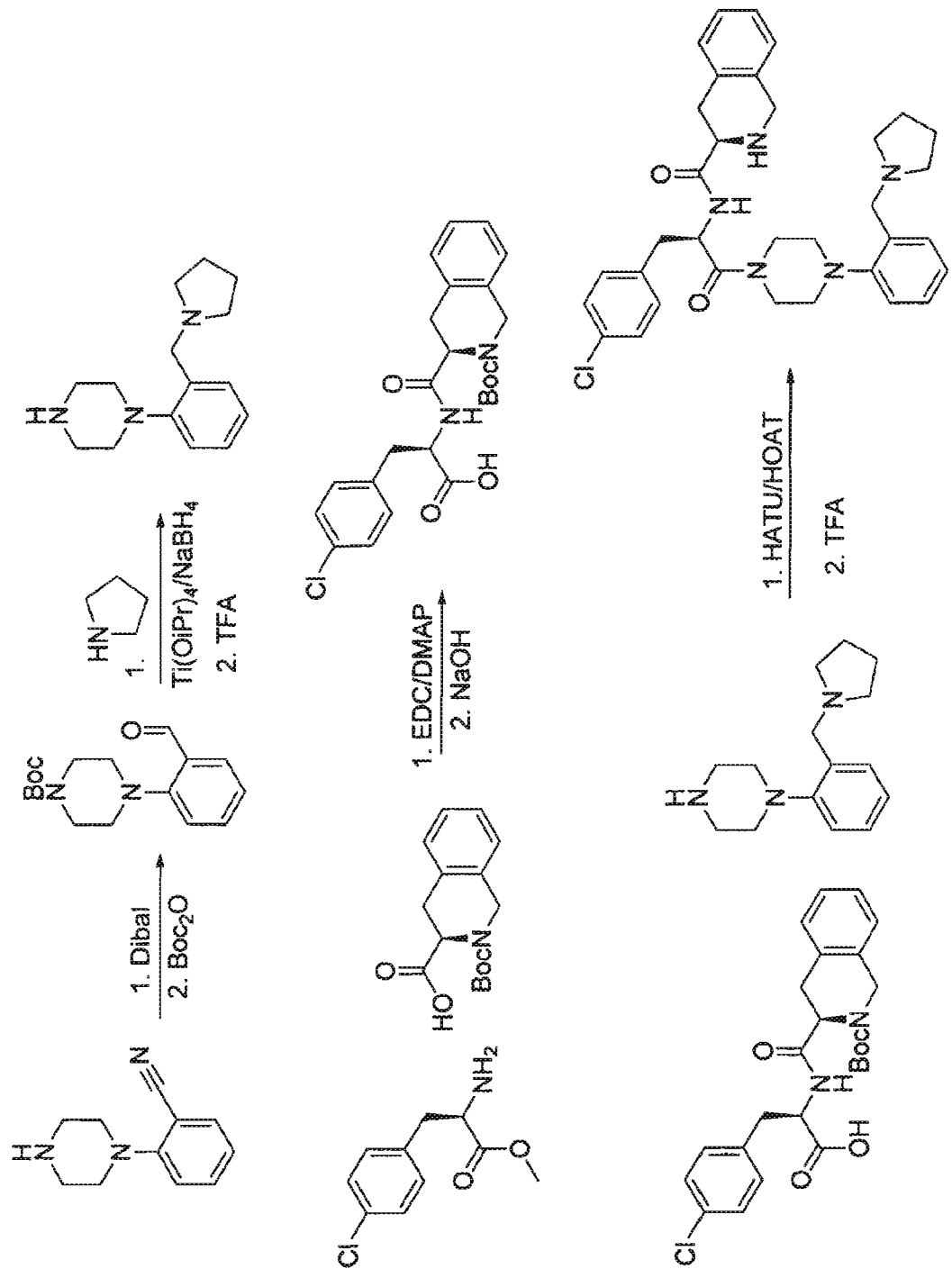
FIG. 4. Synthetic scheme for compound 2.
Figure 5:
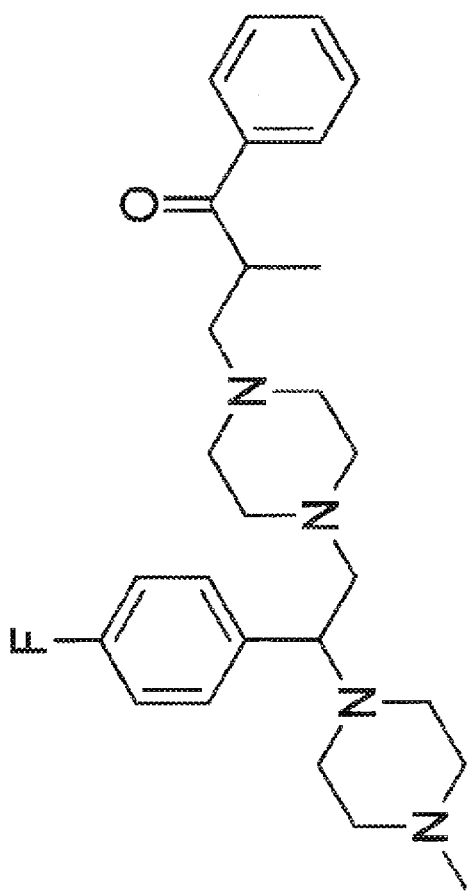
FIG. 5. An antagonist of MC4R, as reported by Arasingham, 2003, *J Med Chem* 46, 9-11 (compound 3).
Figure 7:
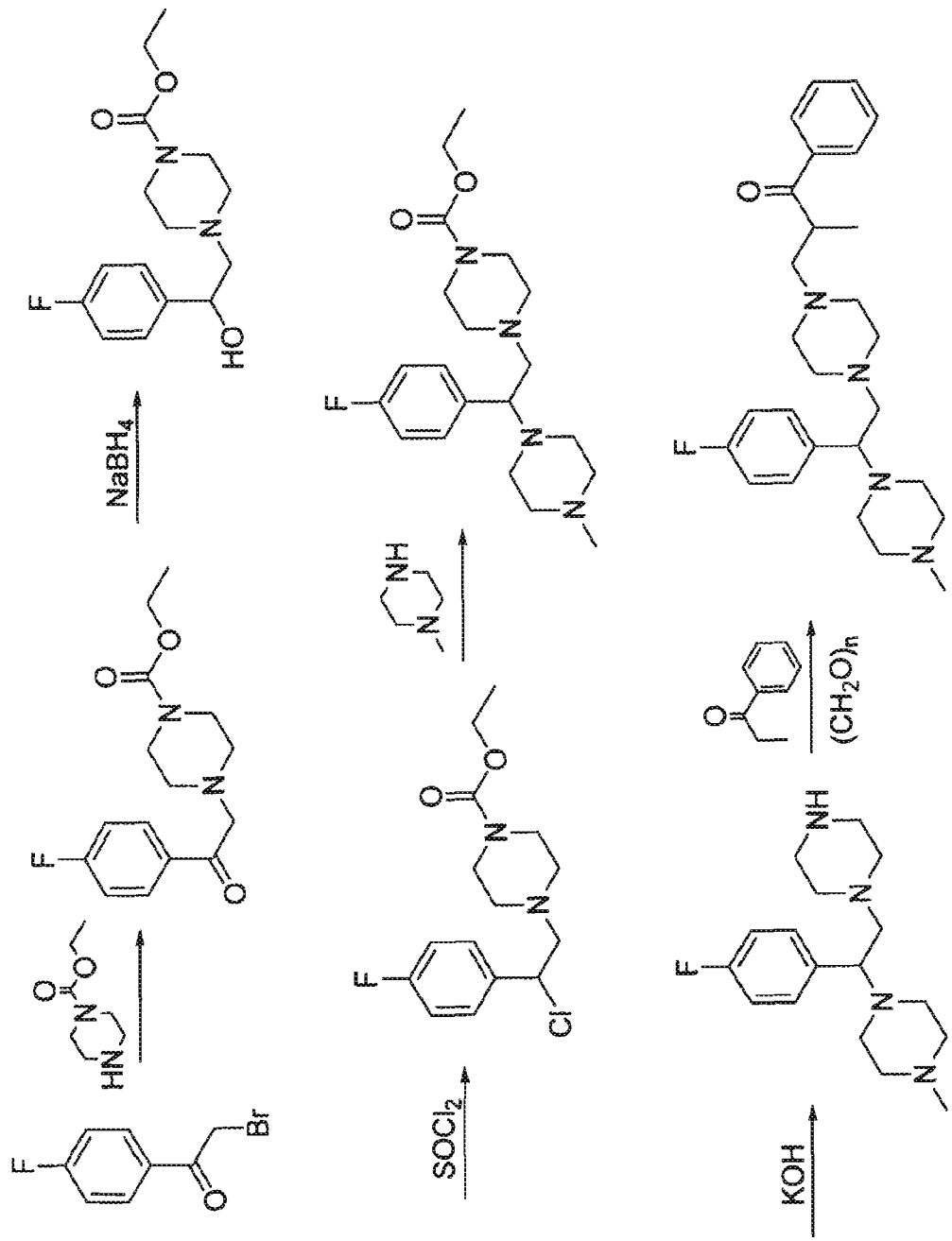
FIG. 7. Synthetic scheme for compound 3.

Synthesis of this molecule (11-steps) was performed based on the scheme depicted in FIG. 4.

c) Synthesis of the Antagonist of FIG. 5 (Compound 3)

Figure 6:
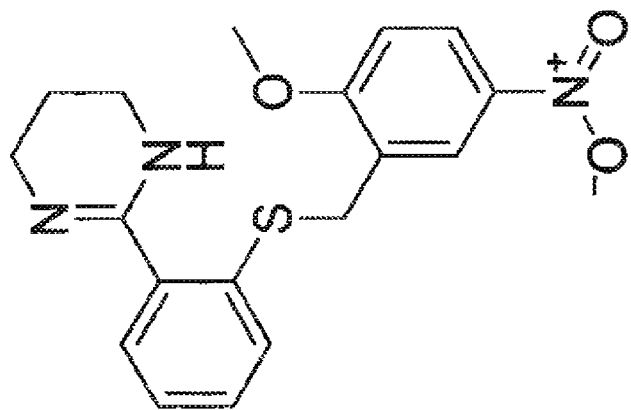
FIG. 6. An antagonist of MC4R (compound 4); the biological activity of this compound is reported in WO 02/062766 using a scintillation proximity assay.

This compound was selected based on the αMSH/MC4R data reported by Arasasingham (*J Bed Chem* 2003, 46: 9-11). Synthesis of this compound was performed according to the method described therein, summarized in FIG. 7.

d) Synthesis of the Antagonist of FIG. 6 (Compound 4)

Figure 8:
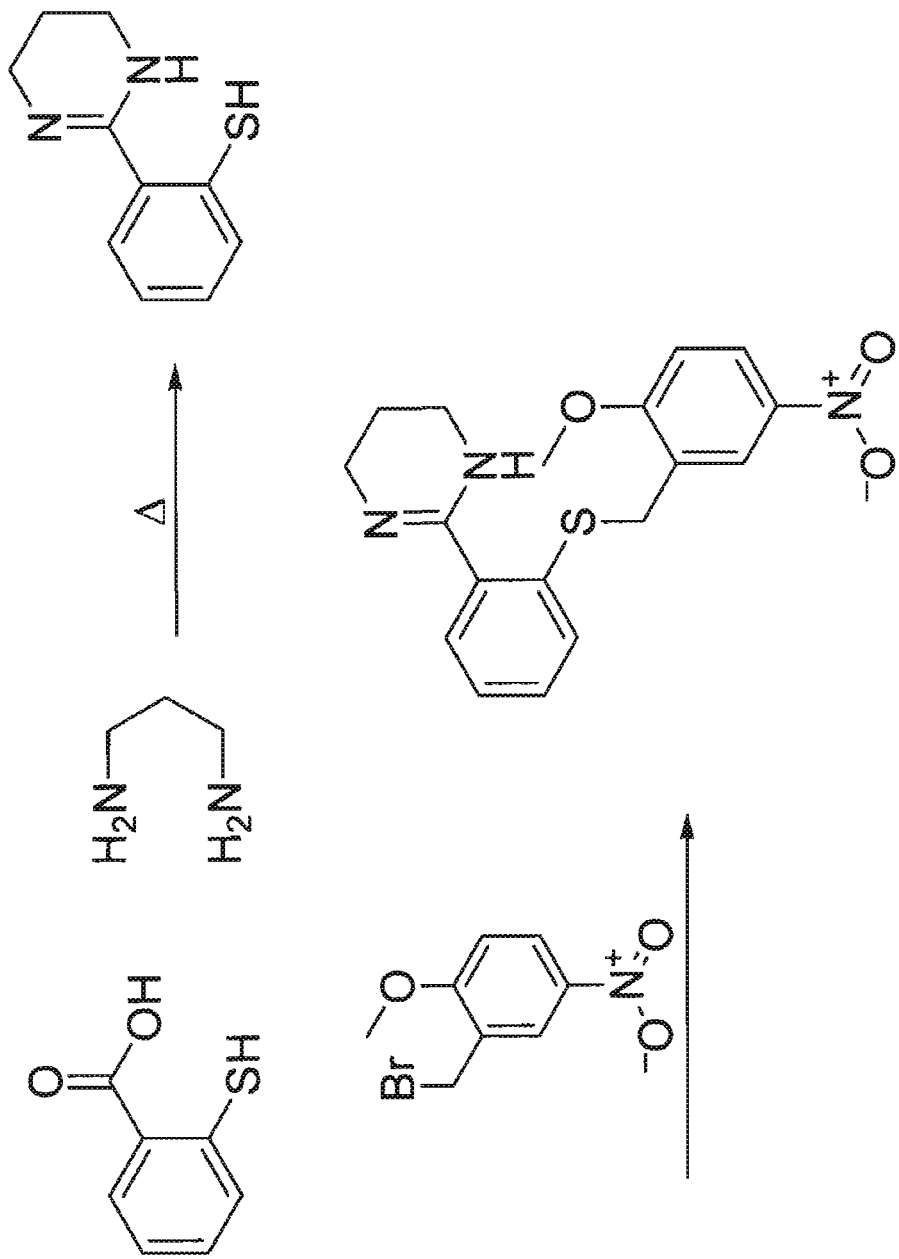
FIG. 8. Synthetic scheme for compound 4.

This compound was selected and synthesized based on the data and synthetic method described in PCT international Patent Publication WO 02/062766 to Millennium Pharmaceuticals; the synthetic scheme is summarized in FIG. 8. The biological activity of this compound is reported in WO 02/062766 using a scintillation proximity assay.

Briefly, synthesis was achieved using the following method:

1,3-diaminopropane (Acros, 27.7 g, 0.374 mmol) is added to thiosalicylic acid (Acros, 20 g, 0.130 mmol) in 1,2-dichlorobenzene (Across 200 ml), this mixture is heated to 170° C. for 4 hours. On cooling to 60° C., methanol (50 ml) is added, the reaction stirs at room temperature overnight and the resulting yellow crystalline solid collected and washed with ether to give 9 g of pure product.

2-Methoxy-5-nitrobenzyl bromide (Fluka, 1.86 g, 7.559 mmol) is added to 2-(1,4,5,6-tetrahydropyrimidin-2-yl)benzenethiol (1 g, 5.201 mmol) in methanol (60 ml) at room temperature, maintained for 12 hours concentrated and ether (10 ml) added, the resulting light yellow needles are collected and washed with ether to give 1.28 g of pure product.

Example 3

Rescue of Misfolded MC4R Using Low Temperature or Chemical Chaperones

Since both low temperatures (thermal rescue) and general chemical chaperones such as DMSO are known to restore folding of mutant proteins, cell surface expression of wild-type and various MC4R folding mutants was evaluated in cells harboring WT and mutant MC4R, and in those cells cultured at 30° C. or with 1% DMSO.

Methods

Cells and Transfections.

HEK 293 cells were transiently transfected with wild-type (WT) or the following hMC4R mutants double tagged with 3HA and Venus (Enhanced Yellow Green Fluorescent Protein; EYFP): S58C; N62S; R165W; R165Q, and P299H.

Low Temperature Assay.

WT and transfected cells were incubated at 30° C. or 37° C. for 12 hours prior to evaluation of MC4R cell surface expression. The gain was determined using the following: Gain=[(% of surface expression at 30° C.−% of surface expression at 37° C.)/% of surface expression at 37° C.]*100.

Chemical Chaperone Assay:

WT and transiently transfected cells were incubated in the presence or absence of 1% DMSO for 12 hours prior to evaluation of MC4R cells surface expression.

FACS Analysis.

FACS analysis was performed after fluorescently labeling cells with primary anti-HA.11 antibody (mouse; 1:1000 dilution) and the secondary antibody coupled to Alexa 647 (goat anti-mouse; 1:1000 dilution) dilution. Live cells (propidium iodide negative) were sorted into the following two relevant populations:

P4: Total YFP positive cells (representative of total MC4R expression)

P5: Percent of cells positive for both YFP and Alexa 647 (Alexa and YFP positive cells)/(YFP positive cells+Alexa and YFP positive cells) (representative of cell surface expression)

Results

MC4R Cell Surface Expression.

Basal surface expression of WT cell surface expression reaches 90%. None of the mutants expressed MC4R on the cell surface as detected by binding of $^{125}$I-labeled NDP-α-MSH (data not shown). When analyzed by FACS, the mutants all exhibited significantly decreased surface expression when compared to cells transfected with WT MC4R (data not shown). About 90% of the WT 3HA-hMC4R-Venus cells exhibited surface expression of MC4R (P5), whereas basal surface expression on the mutants was between 12% and 18% for N62S, R165W, R165Q and P299H. S58C exhibits about 40% surface expression.

Thermal Rescue.

All five mutants exhibited a gain in cell surface expression of MC4R (P5) in Table 2 as follows:

TABLE 2

| Genotype | % Gain |
| --- | --- |
| WT | 12 |
| S585C | 43 |
| N62S | 68 |
| R165W | 63 |
| R165Q | 93 |
| P299H | 107 |

Chemical Chaperone:

No significant enhancement of cell surface expression was detected in the presence of 1% DMSO.

Example 4

Rescue of Misfolded MC4R Using MC4R Pharmacological Chaperones

The MC4R antagonist compounds depicted in FIG. 5 (compound 3) and FIG. 6 (HBr salt; compound 4), respectively were evaluated for chaperone activity in cells harboring the following MC4R mutants: S58C; N62S; R165Q; R165W; and P299H.

Methods

Pharmacological Chaperone Assay.

Briefly, cells harboring each of the above-referenced MC4R mutants (transfected as described in Example 3) were cultured with each of the antagonist compounds at concentrations of 1.0 μM and 10 μM for 12 h and evaluated for cell surface expression of MC4R using fluorescent activated cell sorting analysis as described above. Cell surface expression levels are compared between treatment and basal conditions.

Percent Gain is determined according to the following: [Gain=[(% of surface expression (with treatment)−% of surface expression (w/o treatment))/% of surface expression (w/o treatment)]*100.

MC4R Activity Assay.

Accumulation of cAMP was evaluated for MC4R mutants S58C, N62S, R165W and P299H in response to treatment with MC4R agonist NDP-MSH (10-7M) in the presence or absence of each antagonist using the Catch Point cAMP Fluorescent Assay Kit from Molecular Devices (whole cell assay; Cat. No. R8044). Controls were untreated or treated only with NDP-MSH.

Results

Pharmacological Chaperone Rescue.

As shown in Table 3, below, both antagonists were able to increase surface expression of MC4R mutants R165W, S58C. and R165Q at both 1.0 μM and 10 μM concentrations, with a dose-dependent effect. As indicated above, basal surface expression on the mutants was between 12% and 18% for N62S, R165W, R165Q and P299H. S58C exhibits about 40% surface expression. Unexpectedly, treatment with 10 μM of each compound was able to restore cell surface expression of MC4R R165W to levels identical to cells expressing wild-type MC4R.

For mutant N62 S, no effect was seen at 1.0 μM with either of the compounds, although a significant percent gain in cell surface expression of the mutant MC4R was observed with both compounds at the 10 μM concentration. The compound depicted in FIG. 5 was more potent, i.e., more cell surface expression was observed than with the compound shown in FIG. 6.

For mutant P299H, the compound shown in FIG. 6 had no effect on restoring cell surface expression of the mutant receptor at either 1.0 μM or 10 μM, and only a small effect was observed with the compound shown in FIG. 5 at 10 μM.

TABLE 3

| Compound/ | % Gain | | | | |
| --- | --- | --- | --- | --- | --- |
| concentration | S58C | N62S | R165W | R165Q | P299H |
| 4/10 μM | 130 | 212.5 | 675 | 508 | 38.9 |
| 4/1 μM | 60 | 6.25 | 150 | 91.7 | 11.11 |
| 3/10 μM | 130 | 343.75 | 675 | 508 | 77.78 |
| 3/1 μM | 77.5 | 25 | 467 | 300 | 27.78 |

These results demonstrate that MC4R folding mutants can be "rescued" when contacted with low concentrations of MC4R antagonists, which act as pharmacological chaperones to restore cell surface expression.

Figure 9:
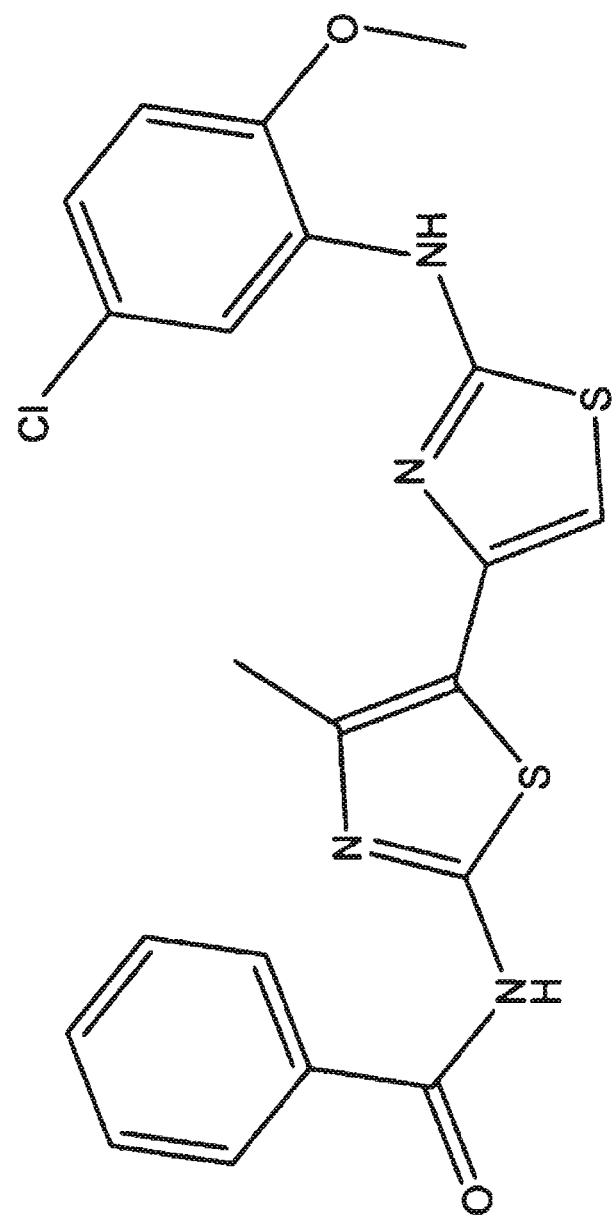
FIG. 9. A bisaminothiazole compound described in Pedemonte et al., *J. Clin. Inves.* 2005; 115: 2564-71 (compound 5).
Figure 10A:
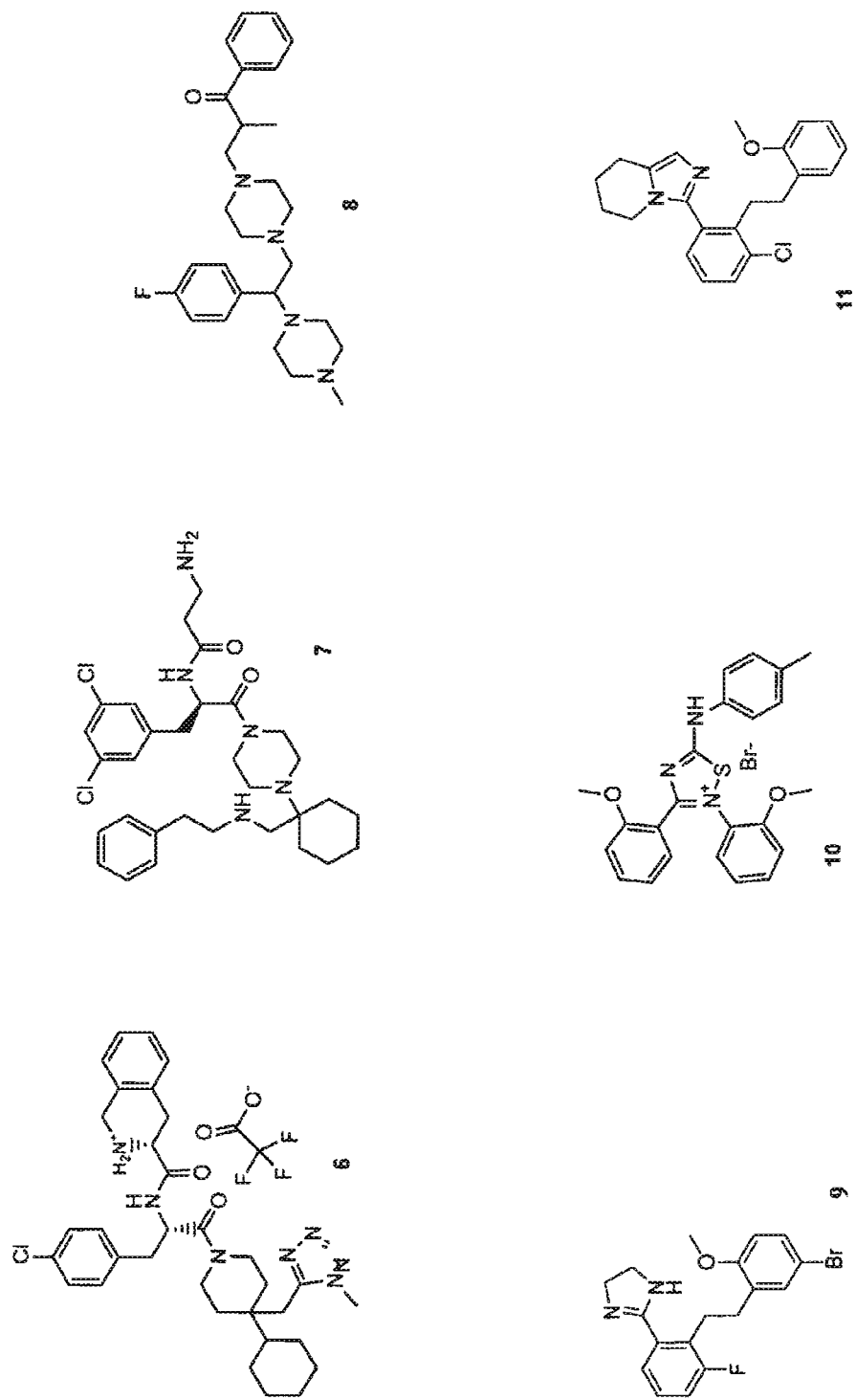
FIG. 10A-D. Compounds 6-25 described infra.
Figure 10B:
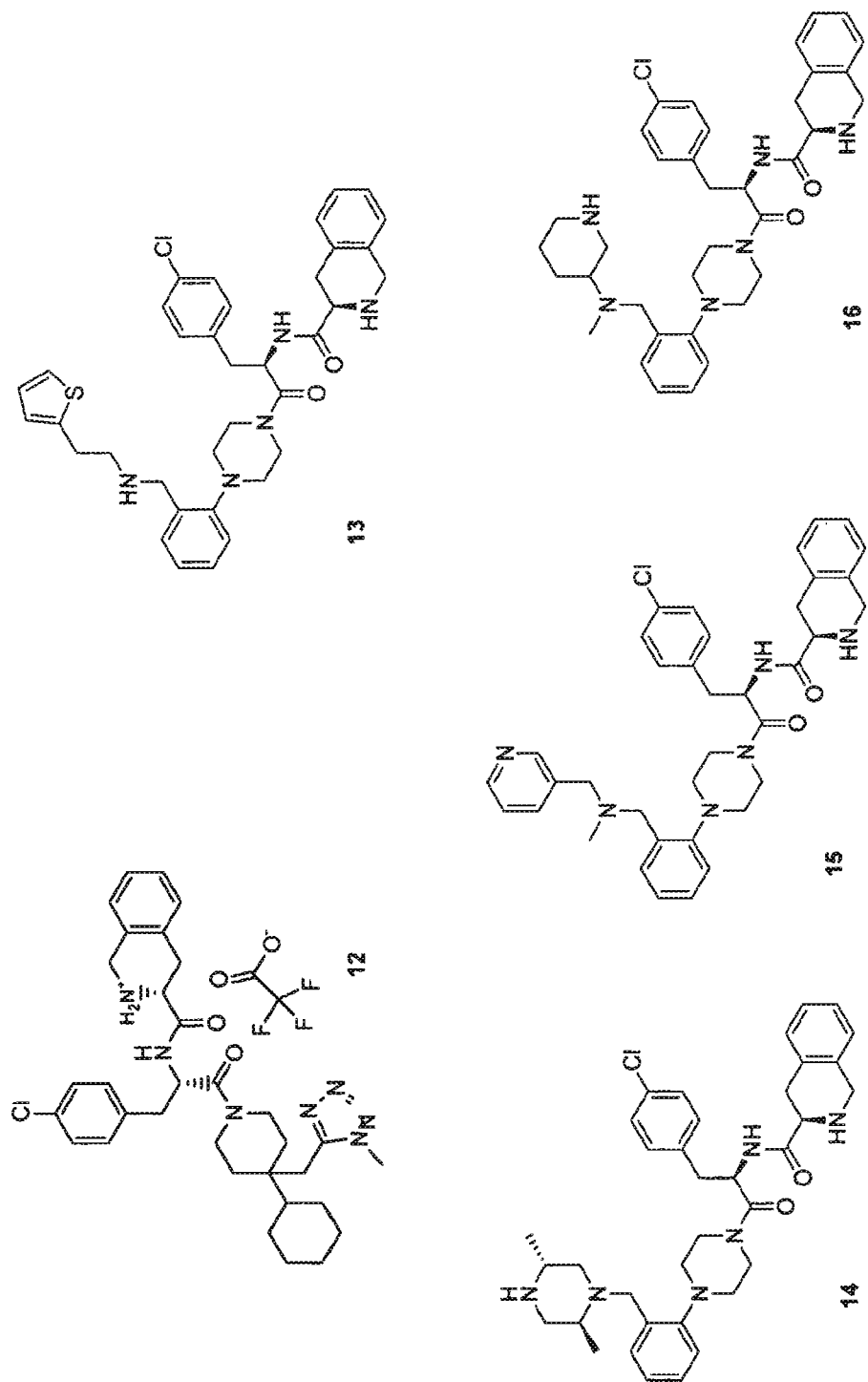
Figure 10C:
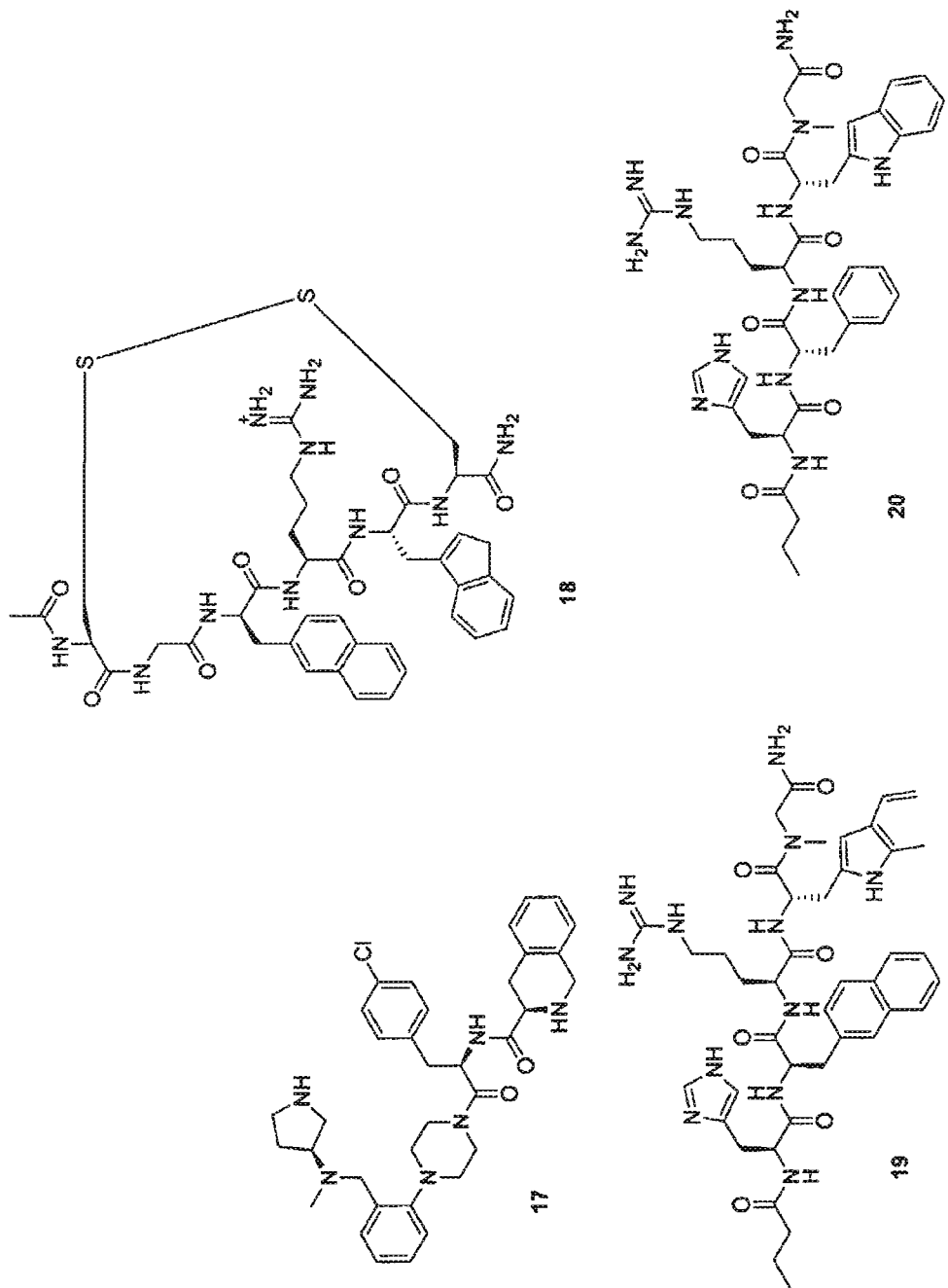
Figure 10D:
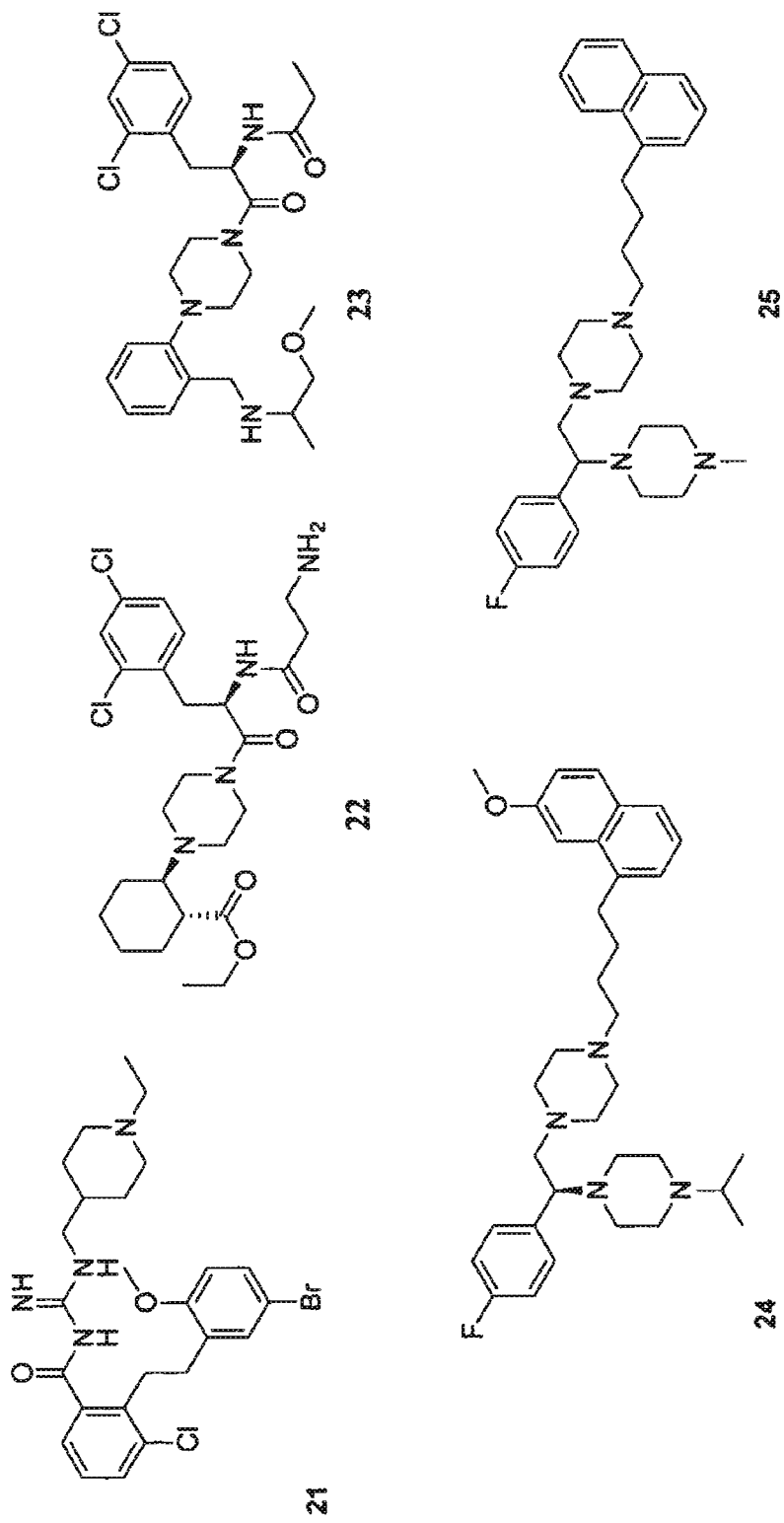

Lastly, a bisaminothiazole compound described in Pedemonte et al., J. Clin. Inves. 2005; 115:2564-71 (FIG. 9) demonstrated a small effect on mutants S58C (31.25% gain) and R165W (28.95% gain).

MC4R Activity.

Figure 11:
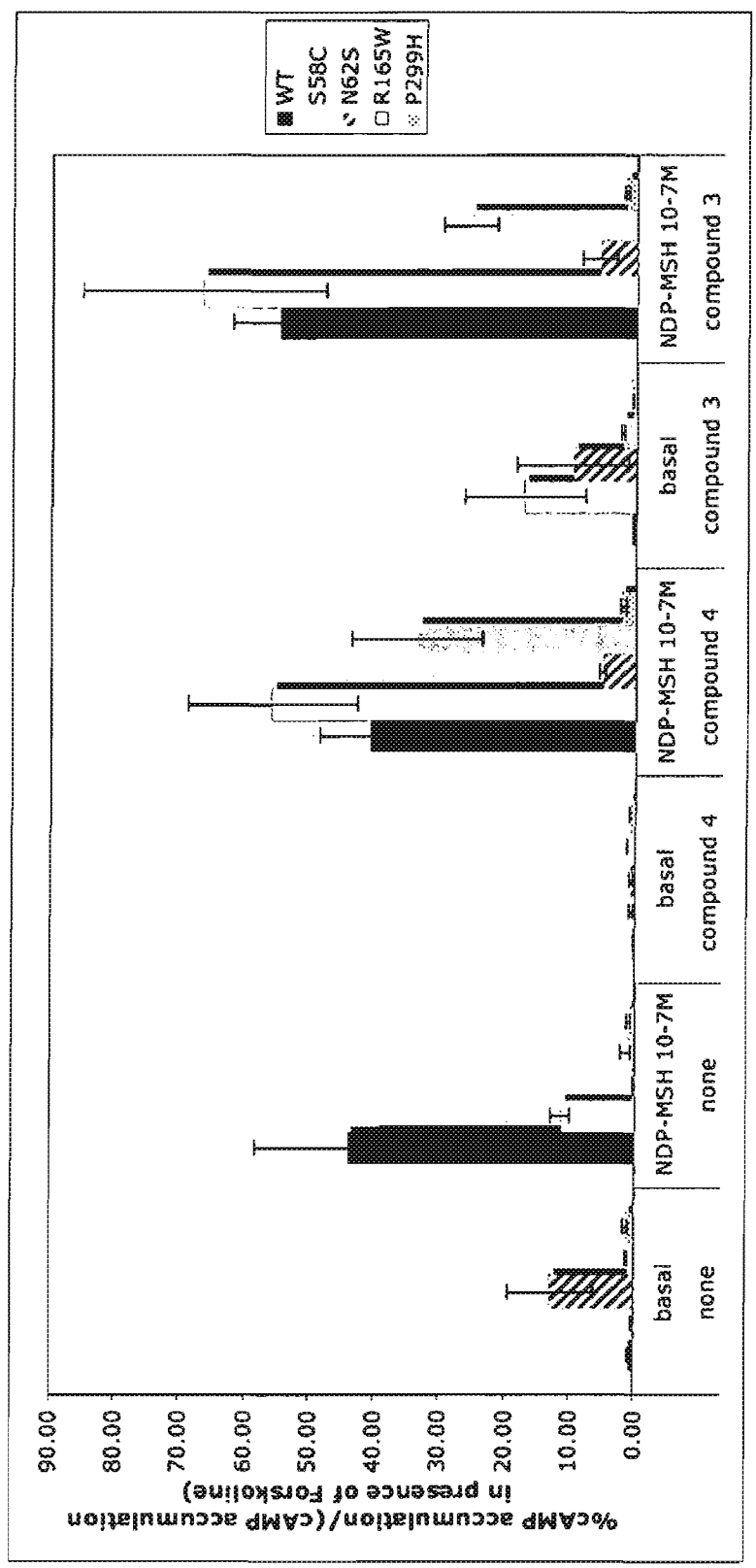
FIG. 11. MC4R signaling assay in MC4R mutants treated with ligand agonist and with and without antagonist chaperones.

As shown in FIG. 11, recovery of signaling through MC4R was observed to the same extent as hMC4R WT in S58C and R165W following treatment with both antagonists at 10 μM. Signaling capacity in MC4R mutant N62S also was restored to a lesser extent. No signaling was restored in P299H, as expected, since this mutation is in a domain necessary for G-protein coupling.

Example 5

Screening for MC4R Chaperones that Restore Stability and Activity of Mutant MC4R or Increase Stability of Wild-Type MC4R This example describes a method for screening for MC4R chaperone compounds for enhancing misfolded mutant or wild-type cell surface expression and/or activity of MC4R.

Methods

Transfection of Mutant or Wild-Type MC4R.

Identification of folding/trafficking MC4R mutants is achieved as described in Example 1. Transfection of such folding mutants and/or wild-type MC4R is achieved as described above, or by using any methods known in the art. Success of transfection is determined by detecting cell surface expression of proteins, such as by FACS analysis.

Chaperone Administration.

To cultures or arrays of MC4R wild-type-expressing or folding-mutant-expressing cells are added various concentrations of chaperone test compounds. The cellular localization of MC4R is then determined, in addition to the activity of the MC4R that is trafficked to the cell surface. For example, piperazine-, piperidine-, 1,4-diazepane-, guanidine-based, or other test compounds as described e.g., in the following are screened: Bednarek and Fong, *Exp Opn Ther Patents* 2004; 14: 327-36; Ujjainwalla et al., *Bioorg. Med. Chem. Lett.* 2003; 13: 4431-4435; WO03/07949; WO03/61660; WO03/09847; WO03/09850; WO03/31410; WO03/94918; WO03/68738; WO03/92690; WO03/93234; WO03/72056; WO03/66597; WO03/66587; WO03/53927; WO02/67869; WO02/68387; WO03/68738; WO02/00259; WO02/92566; WO02/81443; WO02/81430; and WO02/80896.

Detection of Trafficking of MC4R to the Cell Surface.

Detection of cellular and/or cell surface localization of compound-treated MC4R-expressing cells compared to untreated cells is achieved as described above.

Detection of MC4R Activity by Measuring cAMP Accumulation.

48 h after transfection, cells are washed once with PBS and then detached from the plate with PBS containing 0.02% EDTA (Sigma). The detached cells are harvested by centrifugation and resuspended in Hanks' balanced salt solution (Invitrogen) containing 0.5 mM IBMX, 2 mM HEPES, pH 7.5 (IBMX buffer). After incubation at 37° C. for 15 min to allow for IBMX uptake, 0.4 ml of cell suspension (about $5 \times 10^5$ cells/ml are added to 0.1 ml of IBMX buffer containing various concentrations of agonists (e.g., [Nle4-D-Phe7]-MSH (NDP-MSH), α-MSH), or other chaperone candidates or 10 µM forskolin. The cells are subsequently incubated at 37° C. for 15 min to allow for cAMP accumulation. The activity is terminated by adding 0.5 ml of 5% trichloroacetic acid, and cAMP released from lysed cells is assayed by the cAMP $^{125}$I scintillation proximity assay system (Amersham Biosciences). $EC_{50}$ values are calculated with a 95% confidence interval using GraphPad Prism software (using nonlinear regression analysis fitted with a sigmoidal dose-response curve with variable slope).

Example 6

Administration of Single Dose DGJ to Evaluate Safety, Tolerability, Pharmacokinetics, and Effects on α-Galactosidase A Enzymatic Activity This example describes a randomized, double blind, placebo controlled Phase I study of twice daily oral doses of DGJ to evaluate the safety, tolerability, pharmacokinetics, and α-Galatosidase A (α-Gal A) enzymatic activity effects of DGJ in healthy volunteers.

Study Design and Duration.

This study was first-in-man, single-center, Phase I, randomized, double-blind, twice-daily dose, placebo-controlled study to evaluate the safety, tolerability, pharmacokinetics, and α-Gal A enzymatic activity effects of DGJ following oral administration. The study tested two groups of 8 subjects (6 active and 2 placebo) who received a twice-daily dose of 50 or 150 mg of DGJ or placebo administered orally for seven consecutive days, accompanied by a seven day follow up visit. Subjects were housed in the treatment facility from 14 hours prior to dosing until 24 hours after dosing. Meals were controlled by schedule and subjects remained abulatory for 4 hours post drug administration.

Pharmacokinetic parameters were calculated for DGJ in plasma on Day 1 and Day 7. In addition, the cumulative percentage of DGJ excreted (12 hours post dose) in urine was calculated. α-Gal A activity was calculated in white blood cells (WBC) before dosing began, and again at 100 hours, 150 hours, and 336 hours into the trial.

Study Population.

Subjects were healthy, non-institutionalized, non-smoking male volunteers between 19 and 50 years of age (inclusive) consisting of members of the community at large.

Safety and Tolerability Assessments.

Safety was determined by evaluating vital signs, laboratory parameters (serum chemistry, hematology, and urinalysis), ECGs, physical examination and by recording adverse events during the Treatment Period.

Pharmacokinetic Sampling.

Blood samples (10 mL each) were collected in blood collection tubes containing EDTA before dosing and at the following times thereafter: (0.25, 0.5, 0.75, 1, 1.5, 2, 3, 4, 5, 6, 7, 8, 9, 10, 11 and 12 hours. Blood samples were cooled in an ice bath and centrifuged under refrigeration as soon as possible. Plasma samples were divided into two aliquots and stored at 20±10° C. pending assay. At the end of the study, all samples were transferred to MDS Pharma Services Analytical Laboratories (Lincoln) for analysis. The complete urine output was collected from each subject for analysis of DGJ to determine renal clearance for the first 12 hours after administration of DGJ on days 1 and 7.

WBC α-GAL A Enzymatic Activity Sampling.

Blood samples (10 mL each) were collected in blood collection tubes containing EDTA and WBC extracted before dosing and at the following times thereafter: 100 hours, 150 hours, and 336 hours. Samples were treated as described above, and WBC α-Gal A enzymatic activity levels were determined.

Statistical Analysis.

Safety data including laboratory evaluations, physical exams, adverse events, ECG monitoring and vital signs assessments were summarized by treatment group and point of time of collection. Descriptive statistics (arithmetic mean, standard deviation, median, minimum and maximum) were calculated for quantitative safety data as well as for the difference to baseline. Frequency counts were compiled for classification of qualitative safety data.

Adverse events were coded using the MedDRA version 7.0 dictionary and summarized by treatment for the number of subjects reporting the adverse event and the number of adverse events reported. A by-subject adverse event data listing including verbatim term, coded term, treatment group, severity, and relationship to treatment was provided. Concomitant medications and medical history were listed by treatment.

Pharmacokinetic parameters were summarised by treatment group using descriptive statistics (arithmetic means, standard deviations, coefficients of variation, sample size, minimum, maximum and median).

Results

No placebo-treated subjects had an adverse event (AE) and no subject presented with AEs after receiving 50 mg b.i.d. or 150 mg b.i.d. DGJ. DGJ appeared to be safe and well tolerated by this group of healthy male subjects as doses were administered at 50 mg b.i.d. and 150 mg b.i.d.

Laboratory deviations from normal ranges occurred after dosing, but none was judged clinically significant. There were no clinically relevant mean data shifts in any parameter investigated throughout the course of the study. No clinically relevant abnormality occurred in any vital sign, ECG, or physical examination parameter.

Pharmacokinetic Evaluation.

The following table summarizes the pharmacokinetic data obtained during study.

TABLE 4

|  | 50 mg b.i.d. dose | | 150 mg b.i.d. dose | |
|---|---|---|---|---|
|  | Day 1 | Day 7 | Day 1 | Day 7 |
| Cmax (µM) | 2.3 ± 0.3 | 3.9 ± 0.5 | 11.3 ± 1.5 | 10.8 ± 1.4 |
| tmax (h) | 2.9 ± 0.4 | 2.5 ± 0.4 | 3.1 ± 0.4 | 2.9 ± 0.4 |
| $t_{1/2}$ (h) | 2.5 ± 0.1 |  | 2.4 ± 0.05 |  |
| Cmin (µM) |  | 0.4 ± 0.03 |  | 1.2 ± 0.1 |
| 12 h cumulative renal excretion (%)$^a$ | 16 ± 6 | 48 ± 7 | 42 ± 7 | 60 ± 5 |

$^a$Cumulative percentage of DGJ excreted over the 12-hour post dose period.

The pharmacokinetics of DGJ were well characterized in all subjects and at all dose levels. On average, peak concentrations occurred at approximately 3 hours for all dose levels. $C_{max}$ of DGJ increased in a dose-proportional manner when doses were increased from 50 mg to 150 mg.

The mean elimination half-lives ($t_{1/2}$) were comparable at dose levels of 50 and 150 mg on Day 1 (2.5 vs. 2.4 hours).

The mean percentage of DGJ excreted over the 12-hour post dose period was 16% and 42% at dose levels of 50 mg and 150 mg, respectively, on Day 1, increasing to 48% and 60%, respectively, on Day 7.

α-Galactosidase A (α-Gal A) Enzymatic Activity.

The α-Gal A enzymatic activity data obtained during the study is shown in FIG. 1. DGJ did not inhibit WBC α-Gal A enzymatic activity in subjects at dosages of 50 mg b.i.d. or 150 mg b.i.d. Furthermore, DGJ produced a dose-dependent trend of increased WBC α-Gal A activity in healthy volunteers. α-Gal A enzymatic activity was measured in WBC of subjects administered placebo, 50 mg b.i.d., and 150 mg b.i.d. DGJ. Placebo had no effect on WBC α-Gal A enzymatic activity. Variations in enzymatic activity in response to placebo were not clinically significant. Both 50 mg b.i.d. and 150 mg b.i.d. DGJ increased normalized WBC α-Gal A enzymatic activity. In response to 50 mg b.i.d. DGJ, WBC α-Gal A enzymatic activity increased to 120%, 130%, and 145% pre-dose levels at 100 hours, 150 hours, and 336 hours post-dose, respectively. In response to 150 mg b.i.d. DGJ, WBC α-Gal A enzymatic activity increased to 150%, 185%, and 185% pre-dose levels at 100 hours, 150 hours, and 336 hours post-dose, respectively.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A method for treating obesity in an individual having a mutant MC4R polypeptide comprising:
administering to an individual a pharmacological chaperone that binds to the mutant MC4R polypeptide in an amount effective to increase mutant MC4R activity, wherein the pharmacological chaperone is an MC4R polypeptide antagonist having the following structure:

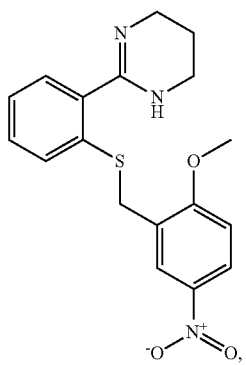

wherein the mutant MC4R polypeptide comprises a mutation selected from the group consisting of P78L, R165Q, R165W, T11A, A175T, I316L, I316S, I317T, N97D, G98R, C271R, S58C, Y157S, I102S, L106P, L250Q, and Y287X.

2. The method of claim 1, wherein the mutant MC4R polypeptide comprises a mutation associated with misfolding of the MC4R polypeptide.

3. The method of claim 1, wherein the pharmacological chaperone binds to the mutant MC4R polypeptide as it is being folded into a functional conformation.

4. The method of claim 1, wherein the activity increased by the pharmacological chaperone is adenylyl cyclase activation.

5. The method of claim 1, wherein the pharmacological chaperone increases MC4R cell surface expression.

6. The method of claim 1, wherein the pharmacological chaperone is administered in a pharmaceutically-acceptable carrier.

7. The method of claim 1, where the pharmacological chaperone is administered orally.

8. The method of claim 1, wherein the mutant MC4R polypeptide comprises the mutation R165Q, R165W, or S58C.

9. A method for treating obesity in an individual having a mutant MC4R polypeptide comprising:
administering to an individual a pharmaceutical chaperone that binds to a mutant MC4R polypeptide in an amount effective to increase mutant MC4R cell surface expression, wherein the pharmacological chaperone is an MC4R polypeptide antagonist having the following structure:

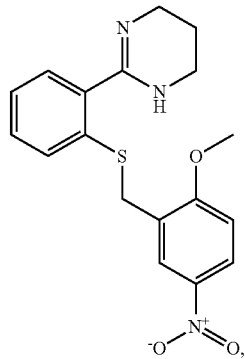

wherein the mutant MC4R polypeptide comprises a mutation selected from the group consisting of P78L, R165Q, R165W, T11A, A175T, I316L, I316S, I317T, N97D, G98R, C271R, S58C, Y157S, I102S, L106P, L250Q, and Y287X.

10. The method of claim 9, wherein the pharmacological chaperone is administered in a pharmaceutically-acceptable carrier.

11. The method of claim 9, wherein the pharmacological chaperone is administered orally.

12. The method of claim 9, wherein the mutant MC4R polypeptide comprises the mutation R165Q, R165W, or S58C.

13. A method for treating obesity in an individual having a mutant MC4R polypeptide comprising:
administering to an individual a pharmacological chaperone that binds to a mutant MC4R polypeptide in an amount effective to increase trafficking of the mutant MC4R polypeptide to the cell membrane, wherein the pharmacological chaperone is an MC4R polypeptide antagonist having the following structure:

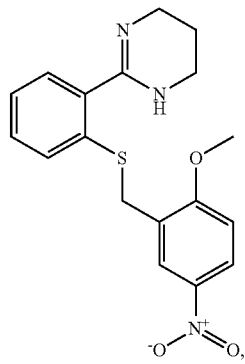

wherein the mutant MC4R polypeptide comprises a mutation selected from the group consisting of P78L, R165Q, R165W, T11A, A175T, I316L, I316S, I317T, N97D, G98R, C271R, S58C, Y157S, I102S, L106P, L250Q, and Y287X.

14. The method of claim 13, wherein the pharmacological chaperone is administered in a pharmaceutically-acceptable carrier.

15. The method of claim 13, wherein the pharmacological chaperone is administered orally.

16. The method of claim 13, wherein the mutant MC4R polypeptide comprises the mutation R165Q, R165W, or S58C.

* * * * *